(12) United States Patent
Vernier et al.

(10) Patent No.: US 8,722,929 B2
(45) Date of Patent: May 13, 2014

(54) N-[2-AMINO-4-(PHENYLMETHOXY)PHENYL] AMIDES AND RELATED COMPOUNDS AS POTASSIUM CHANNEL MODULATORS

(75) Inventors: Jean-Michel Vernier, Laguna Niguel, CA (US); Jianlan Song, Cerritos, CA (US); Huanming Chen, Irvine, CA (US); Zhi Hong, Irvine, CA (US)

(73) Assignee: Valeant Pharmaceuticals International, Bridgewater, NJ (US)

( * ) Notice: Subject to any disclaimer, the term of this patent is extended or adjusted under 35 U.S.C. 154(b) by 1567 days.

(21) Appl. No.: 11/870,368

(22) Filed: Oct. 10, 2007

(65) Prior Publication Data

US 2008/0188561 A1 Aug. 7, 2008

Related U.S. Application Data

(60) Provisional application No. 60/851,084, filed on Oct. 10, 2006, provisional application No. 60/850,867, filed on Oct. 10, 2006.

(51) Int. Cl.
| C07C 233/00 | (2006.01) |
| C07C 235/00 | (2006.01) |
| C07C 237/00 | (2006.01) |
| C07C 239/00 | (2006.01) |

(52) U.S. Cl.
USPC ............ 564/123; 564/218; 564/219; 564/221

(58) Field of Classification Search
USPC .................................. 564/123, 218, 219, 221
See application file for complete search history.

(56) References Cited

U.S. PATENT DOCUMENTS

| | | | |
|---|---|---|---|
| 4,181,803 A | 1/1980 | Morita et al. |
| 4,554,281 A | 11/1985 | vonBebenburg et al. |
| 4,668,684 A | 5/1987 | Tibes et al. |
| 4,778,799 A | 10/1988 | Tibes et al. |
| 4,923,858 A | 5/1990 | Engel et al. |
| 4,923,974 A | 5/1990 | Ueda et al. |
| 5,032,591 A | 7/1991 | Evans et al. |
| 5,162,346 A | 11/1992 | Lobisch et al. |
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 7/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 5,965,582 A | 10/1999 | Lebaut et al. |
| 6,117,900 A | 9/2000 | Rundfeldt et al. |
| 6,211,171 B1 | 4/2001 | Sawynok et al. |
| 6,218,411 B1 | 4/2001 | Koga |
| 6,265,417 B1 | 7/2001 | Carroll |
| 6,281,211 B1 | 8/2001 | Cai et al. |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |
| 6,538,004 B2 | 3/2003 | Drizin |

(Continued)

FOREIGN PATENT DOCUMENTS

| CA | 2542434 | 5/2005 |
| DE | 3337593 | 10/1983 |

(Continued)

OTHER PUBLICATIONS

Vippagunta et al. 2001, "Crystalline Solids." Advanced Drug Delivery Reviews, vol. 48, pp. 3-26.*

Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).

Armijo et al., "Ion channels and epilepsy," *Curr Pharm Des.* 11:1975-2003 (2005).

Barhanin, M., et al., "K,LQT1 and ISK (minK) proteins associate to form the $I_{Ks}$ cardiac potassium current," *Nature* 384(6604):78-80 (1996).

Beeby et al. "The synthesis and properties of 2:7-Disubstituted 1:2:3:4-tetrahydroisoquinolines," *J. Chem. Soc.* ¶ 385, 1799-1803 (1949).

Bialer et al., "Progress report on new antiepileptic drugs: a summary of the fourth Eilat conference (EILAT IV)," *Epilepsy Res.* 34:1-41 (1999).

(Continued)

*Primary Examiner* — Kara R McMillian
(74) *Attorney, Agent, or Firm* — Jones Day

(57) ABSTRACT

This invention provides compounds of formula A and formula B

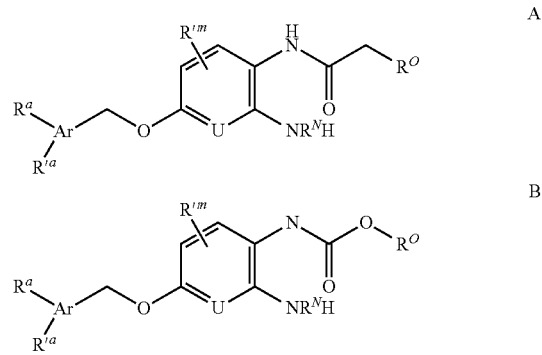

which are modulators of potassium ion channels and are useful for the treatment of seizure disorders.

6 Claims, No Drawings

(56) References Cited

U.S. PATENT DOCUMENTS

| | | | |
|---|---|---|---|
| 6,538,151 | B1 | 3/2003 | Meisel et al. |
| RE38,115 | E | 5/2003 | Smith et al. |
| 6,589,986 | B2 | 7/2003 | Bowlby et al. |
| 6,593,335 | B1 | 7/2003 | Carroll |
| 6,642,209 | B1 | 11/2003 | Fukunuga |
| 6,645,521 | B2 | 11/2003 | Cassel |
| 6,737,422 | B2 | 5/2004 | McNaughton-Smith et al. |
| 6,762,320 | B2 | 7/2004 | Jolidon et al. |
| 6,831,087 | B2 | 12/2004 | Alanine et al. |
| 7,045,551 | B2 | 5/2006 | Wu et al. |
| 7,160,684 | B2 | 1/2007 | Argentieri et al. |
| 7,250,511 | B2 | 7/2007 | Bavetsias |
| 7,309,713 | B2 | 12/2007 | Rundfeldt et al. |
| 7,419,981 | B2 | 9/2008 | Field et al. |
| 7,786,146 | B2 | 8/2010 | Vernier et al. |
| 2002/0013349 | A1 | 1/2002 | Wickenden |
| 2002/0015730 | A1 | 2/2002 | Hoffmann et al. |
| 2002/0183395 | A1 | 12/2002 | Argentieri |
| 2004/0198724 | A1 | 10/2004 | McNaughton-Smith et al. |
| 2005/0089473 | A1 | 4/2005 | Black et al. |
| 2005/0089559 | A1 | 4/2005 | Szelenyi |
| 2005/0090547 | A1 | 4/2005 | Szelenyi |
| 2005/0202394 | A1 | 9/2005 | Dobson |
| 2005/0277579 | A1 | 12/2005 | Krishnan et al. |
| 2006/0155121 | A1 | 7/2006 | Tornoe et al. |
| 2006/0167087 | A1 | 7/2006 | Greve et al. |
| 2007/0066612 | A1 | 3/2007 | Khanzhin et al. |
| 2008/0139610 | A1 | 6/2008 | Vernier et al. |
| 2009/0170885 | A1 | 7/2009 | Vernier et al. |
| 2011/0039827 | A1 | 2/2011 | Blackburn et al. |
| 2011/0104315 | A1 | 5/2011 | Sun et al. |

FOREIGN PATENT DOCUMENTS

| | | | |
|---|---|---|---|
| DE | 3604575 | A1 | 8/1986 |
| DE | 103 49 729.3 | | 10/2003 |
| DE | 103 59 335 | | 5/2005 |
| EP | 1 89 788 | A1 | 8/1986 |
| EP | 0 343 429 | | 5/1989 |
| EP | 1 334 972 | | 8/2003 |
| EP | 1 407 768 | | 4/2004 |
| EP | 1 813 285 | A1 | 8/2007 |
| JP | 2000 14350 | | 5/2000 |
| JP | 2000 143510 | A | 5/2000 |
| RU | 2006117525 | | 12/2005 |
| WO | 98/49152 | | 11/1998 |
| WO | WO 00/55137 | | 9/2000 |
| WO | WO 00/59487 | A2 | 10/2000 |
| WO | WO 00/59508 | A1 | 10/2000 |
| WO | WO 01/01970 | | 1/2001 |
| WO | WO 01/01970 | A2 | 1/2001 |
| WO | WO 01/09612 | | 2/2001 |
| WO | WO 01/22953 | A2 | 4/2001 |
| WO | WO 02/080898 | | 10/2002 |
| WO | WO 03/020706 | | 3/2003 |
| WO | WO 03/097586 | | 11/2003 |
| WO | WO 03/106454 | A1 | 12/2003 |
| WO | WO 2004/058739 | | 7/2004 |
| WO | WO 2004/080950 | | 9/2004 |
| WO | WO 2004/082677 | | 9/2004 |
| WO | WO 2004/096767 | | 11/2004 |
| WO | WO 2004/105795 | | 12/2004 |
| WO | WO 2005/039576 | A1 | 5/2005 |
| WO | WO 2005/048975 | | 6/2005 |
| WO | WO 2005/087754 | | 9/2005 |
| WO | WO 2005/100349 | | 10/2005 |
| WO | WO 2006/029623 | | 3/2006 |
| WO | WO 2006/092143 | | 9/2006 |
| WO | 2008/020607 | | 2/2008 |
| WO | WO 2008/024398 | | 2/2008 |
| WO | WO 2008/066900 | | 6/2008 |

OTHER PUBLICATIONS

Bialer, "Progress report on new antiepileptic drugs: a summary of the Sixth Eilat Conference (EILAT VI)," *Epilepsy Res.* 51:31-71 (2002).

Bialer, "Progress report on new antiepileptic drugs: a summary of the Seventh Eilat Conference (EILAT VII)," *Epilepsy Res.* 61:1-48 (2004).

Biervert et al., "A potassium channel mutation in neonatal human epilepsy," *Science* 279:403-406 (1998).

Blackburn-Munro and Jensen, "The anticonvulsant retigabine attenuates nociceptive behaviours in rat models of persistent and neuropathic pain," *Eur J Pharmacol.* 460: 109-116 (2003).

Brown and Adams, "Muscarinic suppression of a novel voltage-sensitive $K^+$ current in a vertebrate neurone," *Nature* 283:673-676 (1980).

Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 (1998).

Cooper et al., "Colocalization and coassembly of two human brain M-type potassium channel subunits that are mutated in epilepsy," *Proc Natl Acad Sci USA* 97:4914-4919 (2000).

Delmas and Brown, "Pathways modulating neural KCNQ/M (Kv7) potassium channels," *Nat Rev Neurosci.* 6:850-862 (2005).

Dickenson al., "Neurobiology of neuropathic pain: mode of action of anticonvulsants," *Eur. J. Pain* 6:51-60 (2002).

Dost et al., "The anticonvulsant retigabine potently suppresses epileptiform discharges in the low Ca ++ and low Mg++ model in the hippocampal slice preparation," *Epilepsy Res.* 38:53-56 (2000).

Friedel and Fitton, "Flupirtine: a review of its analgesic properties, and therapeutic efficacy in pain states," *Drugs* 45:548-569 (1993).

Hiller et al., "Retigabine N-glucuronidation and its potential role in enterohepatic circulation," *Drug Metab Dispos.* 27(5):605-612 (1999).

Hunt and Mantyh, "The molecular dynamics of pain control," *Nat Rev Neurosci.* 2:83-91 (2001).

Jentsch, "Neuronal KCNQ potassium channels; physiology and role in disease," *Nat. Rev Neurosci.*, 1:21-30 (2000).

Jiang et al., "X-ray structure of a voltage-dependent K+ channel," *Nature* 423:33-41 (2003).

Kharkovets et al., "Mice with altered KCNQ4 $K^+$ channels implicate sensory outer hair cells in human progressive deafness," *EMBO J* 25:642-652 (2006).

Kibbe *Handbook of Pharmaceutical Excipients* (Pharmaceutical Press, London) (2000).

Kubisch et al., "KCNQ4, a novel potassium channel expressed in sensory outer hair cells, is mutated in dominant deafness," *Cell* 96:437-446 (1999).

Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J Neurosci.*, 9:605-616 (1997).

Lee et al., "Structure of the KvAP voltage-dependent $K^+$ channel and its dependence on the lipid membrane," *Proc Natl Acad Sci USA* 102:15441-15446 (2005).

Long et al., "Crystal Structure of a mammalian voltage-dependent *Shaker* family $K^+$ channel," *Science* 309:897-903 (2005).

Main et al., "Modulation of KCNQ2/3 potassium channels by the novel anticonvulsant retigabine," *Mol. Pharmacol.* 58:253-262 (2000).

Marrion, "Control of M-currents," *Annu Rev Physiol.* 59:483-504 (1997).

Parcej and Eckhardt-Strelau, Structural characterization of neuronal voltage-sensitive $K^+$ channels heterologously expressed in *Pichia pastoris, J Mol Biol* 333:103-116 (2003).

Passmore et al., "KCNQ/M currents in sensory neurons: significance for pain therapy," *J. Neurosci.* 23:7227-7236 (2003).

Porter et al., "Retigabine," *Neurotherapeutics* 4:149-154 (2007).

Reich et al., "Design and synthesis of novel 6,7-imidazotetrahydroquinoline inhibitors of thymidylate synthase using iterative protein crystal structure analysis," *J. Med. Chem.* 35:847-858 (1992).

Rogawski, MA, "KCNQ2/KCNQ3 K+ channels and the molecular pathogenesis of epilepsy: implications for therapy," *Trends Neurosci.* 23:393-398 (2000).

(56) References Cited

OTHER PUBLICATIONS

Rostock et al., "A new anticonvulsant with broad spectrum activity in animal models of epileptic seizures," *Epilepsy Res.* 23:211-223 (1996).
Rundfeldt et al., "Multiple actions of the new anticonvulsant D-23129 on voltage-gated inward currents and GABA-induced currents in cultured neuronal cells (abstract)," *Naunyn-Schmiedeberg's Arch Pharmacol* 351 (Suppl):R160 (1995).
Rundfeldt, "Characterization of the K+ channel opening effect of the anti-convulsant retigabine in PC12 cells," *Epilepsy Res.* 35:99-107 (1999).
Rundfeldt, "The new anticonvulsant retigabine (D23129) acts as an opener of $K^+$ channels in neuronal cells," *Eur J Pharmacol.* 336:243-249 (1997).
Schroeder et al., "KCNQ5, a novel potassium channel broadly expressed in brain, mediates M-type currents," *J. Biol. Chem.* 275:24089-24095 (2000).
Schroeder, "Moderate loss of function of cyclic-AMP-modulated KNCQ2/KCNQ3 $K^+$ channels causes epilepsy," *Nature* 396:687-690 (1998).
Singh et al., "A novel potassium channel gene, KCNQ2, is mutated in an inherited epilepsy of newborns," *Nat Genet.* 18:25-29 (1998).
Suzuki and Dickenson, "Neuropathic pain: nerves bursting with excitement," *NeuroReport* 11:R17-R21 (2000).
Tatulian and Brown, "Effect of the KCNQ potassium channel opener retigabine on single KCNQ2/3 channels express in CHO cells," *J Physiol.* 549:57-63 (2003).
Tatulian et al., "Activation of expressed KCNQ potassium currents and native neuronal M-type potassium currents by the anti-convulsant drug retigabine," *J. Neurosci.* 21:5535-5545 (2001).
Tober et al., "D-23129: a potent anticonvulsant in the amygdala kindling model of complex partial seizures," *Eur J Pharmacol,* 303:163-169 (1996).
Von Bebenburg et al., "Substituierte Polyaminopyridine" *Chemiker-Zeitung* 103:387-399 (1979). (German language article attached.).
Wang et al., KCNQ2 and KCNQ3 potassium channel subunits: molecular correlates of the M-channel, *Science* 282:1890-1893 (1998).
Wang et al., "Positional cloning of a novel potassium channel gene: KVLQT1 mutations cause cardiac arrhythmias," *Nat Genet* 12:17-23 (1996).
Watanbe et al., "Disruption of the epilepsy KCNQ2 gene results in neural hyperexcitability," *J. Neurochem* 75:28-33 (2000).
Wickenden et al., "KCNQ potassium channels: drug targets for the treatment of epilepsy and pain," *Exp. Opin Thera Patents* 14(4): 457-469 (2004).
Wickenden et al., "Retigabine, a novel anti-convulsant, enhances activation of KCNQ2/Q3 potassium channels," *Mol. Pharmacol.* 58:591-600 (2000).
Wuttke, "The new anticonvulsant retigabine favors voltage-dependent opening of the Kv7.2 (KCNQ2) channel by binding to its activation gate," *Mol. Pharmacol.* 67:1009-1017 (2005).
Beck et al., "Kreuzschmerzen in der Gynaekologischen praxis," Ginaekologe, Springer Verlag, Berlin Germany 35(5):490-494 (2002).
Kuo et al., "Inhibition of $Na^+$ current by diphenhydramine and other diphenyl compounds: molecular determinants of selective binding to the inactivated channels," *Mol. Pharmacol.* 57(1):135-143 (2000).
Patani, "Bioisosterism: a Rational Approach in Drug Design," *Chem. Rev.* 96:3147-3176 (1996).
Touboul et al. "A Comparative evaluation of the effects of Propafenone and lidocaine on early ventricular arrhythmias after acute myocardial infarction," *Eur. Heart J.* 9:1188-1193 (1988). Abstract.
Vippagunta et al., "Crystalline solids," *Adv. Drug Deliv. Rev.* 48:3-26 (2001).
Wolf (ed.), Burger's Medicinal Chemistry and Drug Discovery, 5th Edition vol. 1: Principles and Practice, John Wiley & Sons, New York, pp. 975-977 (1995).
Wu et al., "Regulatory perspectives of Type II prodrug development and time-dependent toxicity management: nonclinical Pharm/Tox analysis and the role of comparative toxicology," *Toxicology* 236:1-6 (2007).
Zani et al., "Sodium channels are required during in vivo sodium chloride hyperosmolarity to stimulate increase in intestinal endothelial nitric oxide production," *Am. J. Physiol. Heart Circ. Physiol.* 288:H89-H95 (2005).
West, Solid State Chemistry and Its Applications (John Wiley & Sons, New York) pp. 358 and 365 (1988).
Said, "Glutamate receptors and asthmatic airway disease," Trends. Pharmacol. Sci. 20(4):132-134 (1999).
Xue et al., "Rational design, synthesis and structure-activity relationships of a cyclic succinate series of TNF-alpha converting enzyme inhibitors. Part 1: lead identification," Bioorg. Med. Chem. Lett. 13(24):4293-4297 (2003).
Lange et al., "Refinement of the binding site and mode of action of the anticonvulsant Retigabine on KCNQ K+ channels," Mol. Pharmacol. 75(2):272-280 (2009).

\* cited by examiner

N-[2-AMINO-4-(PHENYLMETHOXY)PHENYL] AMIDES AND RELATED COMPOUNDS AS POTASSIUM CHANNEL MODULATORS

CROSS-REFERENCE TO RELATED APPLICATIONS

This application claims priority from U.S. Provisional Application Ser. No. 60/851,084, filed Oct. 10, 2006, and U.S. Provisional Application Ser. No. 60/850,867, also filed Oct. 10, 2006, each of which is incorporated herein by reference.

FIELD OF THE INVENTION

This invention concerns novel compounds that activate or otherwise modulate voltage-gated potassium channels. The compounds are useful for the treatment and prevention of diseases and disorders which are affected by modulation of potassium ion channels. One such condition is seizure disorders.

BACKGROUND OF THE INVENTION

Epilepsy is a well-known neurological disease, found in about 3% of the population. Approximately 30% of patients with epilepsy do not respond to currently available therapies. Such unfortunate patients—who number hundreds of thousands of people world-wide—must contend with both uncontrolled seizures and the resulting narrowing of their options in such crucial areas of life as health insurance, employment, and driving.

Retigabine (N-[2-amino-4-(4-fluorobenzylamino)phenyl] carbamic acid, ethyl ester) (U.S. Pat. No. 5,384,330) has been found to be an effective treatment of seizure disorders and has also been found useful in treating pain. Retigabine has been found to be particularly potent in models for the drug-refractory types of epilepsy. Bialer, M. et al., *Epilepsy Research* 1999, 34, 1-41; Blackburn-Munro and Jensen, *Eur. J. Pharmacol.* 2003, 460, 109-116; Wickenden, A. D. et al., *Expert Opin. Ther. Patents*, 2004, 14(4).

"Benign familial neonatal convulsions," an inherited form of epilepsy, has been associated with mutations in the KCNQ2/3 channels. Biervert, C. et al., *Science* 1998, 27, 403-06; Singh, N. A., et al., *Nat. Genet.* 1998, 18, 25-29; Charlier, C. et al., *Nat. Genet.* 1998, 18, 53-55; Rogawski, *Trends in Neurosciences* 2000, 23, 393-398. Subsequent investigations have established that one important site of action of retigabine is the KCNQ2/3 channel. Wickenden, A. D. et al., *Mol. Pharmacol.* 2000, 58, 591-600; Main, M. J. et al., *Mol. Pharmacol.* 2000, 58, 253-62. Retigabine has been shown to increase the conductance of the channels at the resting membrane potential, with a possible mechanism involving binding of the activation gate of the KCNQ 2/3 channel. Wuttke, T. V., et al., *Mol. Pharmacol.* 2005. Additionally, retigabine has been shown to increase neuronal M currents and to increase the channel open probability of KCNQ 2/3 channels. Delmas, P. and Brown, D. A. *Nat. Revs Neurosci.*, vol. 6, 2005, 850-62; Tatulian, L. and Brown, D. A., *J. Physiol.*, (2003) 549, 57-63.

The seizure type that has been most resistant to therapy is the so-called "complex partial seizure." Retigabine is active in several seizure models, including, as indicated above, models for drug-refractory epilepsy. Because of retigabine's broad spectrum of activity and its unusual molecular mechanism, there is hope that retigabine will be effective in management of several seizure types, including the complex partial seizure, which have been resistant to treatment. Porter, R. J., Nohria, V., and Rundfeldt, C., *Neurotherapeutics*, 2007, vol. 4, 149-154.

The recognition of retigabine as a potassium channel opener has inspired a search among compounds with structural features in common with retigabine for other compounds which can affect the opening of, or otherwise modulate, potassium ion channels.

BRIEF DESCRIPTION OF THE INVENTION

In one embodiment, this invention provides compounds of formula A,

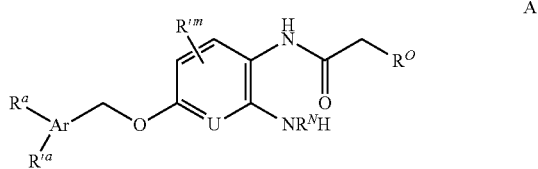

where Ar is phenyl, pyridyl, thienyl, furyl, or benzothienyl; U=—C($R^m$)= or —N=; $R^a$ and $R^{ia}$ are, independently, H, F, Cl, methyl, methoxy, fluoromethyl, difluoromethyl, or trifluoromethyl; $R^{im}$ and $R^m$ are, independently, H, F, Cl, methyl, fluoromethyl, difluoromethyl, trifluoromethyl or methoxy; $R^N$ is H or $C_1$-$C_4$ alkyl, which may be straight-chain, branched, or cyclic; and $R^O$ is H, isopropyl, sec-butyl, or straight-chain $C_1$-$C_8$ alkyl, alkenyl, or alkynyl, any of which may be substituted by methyl, fluoro, chloro methoxy, phenyl, or benzoyloxy, where the methyl, methoxy, phenyl, and benzyl groups are optionally substituted with one or two fluorine atoms or one or two chlorine atoms.

In another embodiment, this invention provides compounds of formula B,

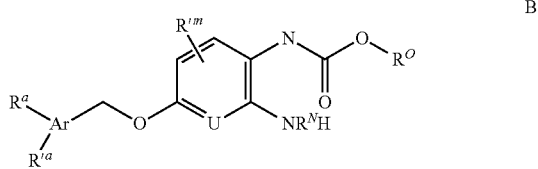

where Ar is phenyl, pyridyl, thienyl, furyl, or benzothienyl; U=—C($R^m$)= or —N=; $R^a$ and $R^{ia}$ are, independently, H, F, Cl, methyl, methoxy, fluoromethyl, difluoromethyl, or trifluoromethyl; $R^{im}$ and $R^m$ are, independently, H, F, Cl, methyl, fluoromethyl, difluoromethyl, trifluoromethyl or methoxy; $R^N$ is H or $C_1$-$C_4$ alkyl, which may be straight-chain, branched, or cyclic; and $R^O$ is isopropyl, sec-butyl, or straight-chain $C_1$-$C_8$ alkyl, alkenyl, or alkynyl, any of which may be substituted by methyl, fluoro, chloro methoxy, phenyl, or benzoyloxy, where the methyl, methoxy, phenyl, and benzyl groups are optionally substituted with one or two fluorine atoms or one or two chlorine atoms.

Compounds of formulas A and B are modulators of potassium ion channels.

In one subgeneric embodiment, this invention provides a compound of formula A-I below

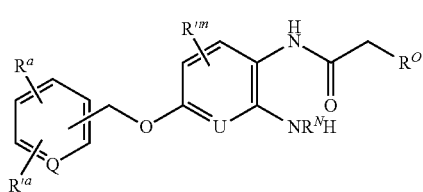

where Q is —CH= or —N=.

In a more specific subgeneric embodiment the invention provides compounds of formula A-II.

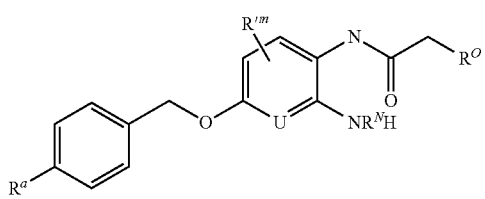

In a still more specific subgeneric embodiment, this invention provides or contemplates a compound of formula A-II where U is —C(R$^m$)=.

In a still more specific subgeneric embodiment, this invention provides or contemplates a compound of formula A-II where U is —C(R$^m$)= and R$^N$ is H, methyl, or ethyl.

In another still more specific subgeneric embodiment, this invention provides or contemplates a compound of formula A-II where U is —CH=.

In another more specific subgeneric embodiment, this invention provides or contemplates a compound of formula A-II where U is —N=.

In another more specific subgeneric embodiment, this invention provides or contemplates a compound of formula A-II where U is —N= and R$^N$ is H, methyl, or ethyl.

In another subgeneric embodiment, the invention provides a compound of formula A-III,

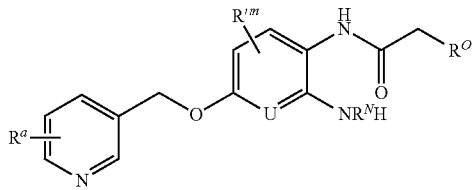

In one more specific subgeneric embodiment, this invention provides or contemplates a compound of formula A-III where U is —C(R$^m$)=.

In another still more specific subgeneric embodiment, this invention provides a compound of formula A-III in which R$^{'m}$ is H.

In another more specific subgeneric embodiment, this invention provides or contemplates a compound of formula A-III where U is —N=.

In another more specific subgeneric embodiment, this invention provides or contemplates a compound of formula A-III where U is —N= and R$^N$ is H, methyl, or ethyl.

In another subgeneric embodiment, the invention provides a compound of formula A-IV,

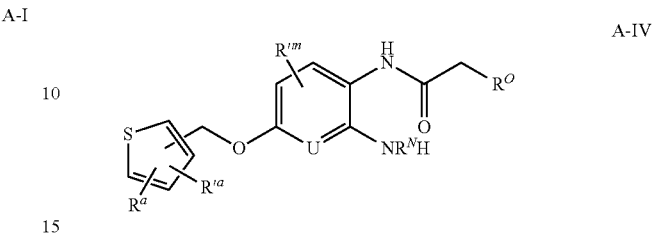

In one more specific subgeneric embodiment, this invention provides or contemplates a compound of formula A-IV where U is —C(R$^m$)= and R$^{'m}$ is H, fluoro, or methyl.

In another still more specific subgeneric embodiment, this invention provides a compound of formula A-IV in which U is —N= and R$^{'m}$ is H, methyl, or fluoro.

In another more specific subgeneric embodiment, this invention provides or contemplates a compound of formula A-IV where U is —N=.

In a still more specific subgeneric embodiment, this invention provides or contemplates a compound of formula A-IV where U is —C(R$^m$)=, R$^{'m}$ is H, methyl, or fluoro, and R$^N$ is H, methyl, or ethyl.

In another more specific subgeneric embodiment, this invention provides or contemplates a compound of formula A-IV where U is —N=, R$^{'m}$ is H or methyl, and R$^N$ is H, methyl, or ethyl.

In another more specific embodiment, this invention provides or contemplates a compound of formula A-IV where R$^a$ is halogen.

In a still more specific embodiment, this invention provides or contemplates a compound of formula A-IV where R$^a$ is halogen and R$^N$ is H, methyl, or ethyl.

In another subgeneric embodiment, the invention provides a compound of formula A-V,

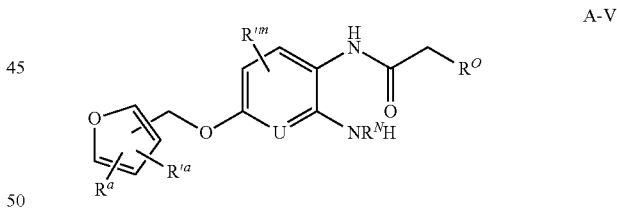

In one more specific subgeneric embodiment, this invention provides or contemplates a compound of formula A-V where U is —C(R$^m$)=.

In another more specific subgeneric embodiment, this invention provides or contemplates a compound of formula A-V where U is —N=.

In one more specific subgeneric embodiment, this invention provides or contemplates a compound of formula A-V where U is —C(R$^m$)= and R$^N$ is H, methyl, or ethyl.

In another more specific subgeneric embodiment, this invention provides or contemplates a compound of formula A-V where U is —N= and R$^N$ is H, methyl, or ethyl.

In one more specific subgeneric embodiment, this invention provides or contemplates a compound of formula A-V where U is —C(R$^m$)=; R$^{'m}$ is H, methyl, or fluoro; and R$^N$ is H, methyl, or ethyl.

In another more specific subgeneric embodiment, this invention provides or contemplates a compound of formula A-V where U is —N═; $R'''$ is H, methyl, or fluoro; and $R^N$ is H, methyl, or ethyl.

In another subgeneric embodiment, the invention provides a compound of formula A-VI, $$\text{A-VI}$$

In one more specific subgeneric embodiment, this invention provides or contemplates a compound of formula A-VI where U is —C($R'''$)═.

In another more specific subgeneric embodiment, this invention provides or contemplates a compound of formula A-VI where U is —N═.

In another, more specific embodiment, this invention provides or contemplates a compound of formula A, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula A, where $R^O$ is benzyloxy alkyl.

In another, more specific embodiment, this invention provides or contemplates a compound of formula A, where $R^O$ is methoxy alkyl.

In another, more specific embodiment, this invention provides or contemplates a compound of formula A, where $R^O$ is phenyl-substituted alkyl.

In another, more specific embodiment, this invention provides or contemplates a compound of formula A, where $R^O$ is benzyloxy alkyl and $R^N$ is H, methyl, or ethyl.

In another, more specific embodiment, this invention provides or contemplates a compound of formula A, where $R^O$ is methoxy alkyl and $R^N$ is H, methyl, or ethyl.

In another, more specific embodiment, this invention provides or contemplates a compound of formula A, where $R^O$ is phenyl-substituted alkyl and $R^N$ is H, methyl, or ethyl.

In another, more specific embodiment, this invention provides or contemplates a compound of formula A, where $R^O$ is isobutyl or tert-butyl.

In another, more specific embodiment, this invention provides or contemplates a compound of formula A, where $R^O$ is isopropyl or sec-butyl.

In another, more specific embodiment, this invention provides or contemplates a compound of formula A, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A, where $R^O$ is $C_2$-$C_8$ alkenyl, optionally substituted.

In another, more specific embodiment, this invention provides or contemplates a compound of formula A, where $R^O$ is $C_2$-$C_8$ alkynyl, optionally substituted.

In another, more specific embodiment, this invention provides or contemplates a compound of formula A, where $R^O$ is 2-propynyl, 3-butynyl, 2-butynyl, propen-2-yl, or buten-3-yl.

In another, more specific embodiment, this invention provides or contemplates a compound of formula A, where $R^N$ is H, methyl, or ethyl.

In another, more specific embodiment, this invention provides or contemplates a compound of formula A, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula A-I, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula A-I, where $R^O$ is isopropyl or sec-butyl.

In another, more specific embodiment, this invention provides or contemplates a compound of formula A-I, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A-I, where $R^O$ is $C_2$-$C_8$ alkenyl, optionally substituted.

In another, more specific embodiment, this invention provides or contemplates a compound of formula A-I, where $R^O$ is $C_2$-$C_8$ alkynyl, optionally substituted.

In another, more specific embodiment, this invention provides or contemplates a compound of formula A-I, where $R^O$ is 2-propynyl, 3-butynyl, 2-butynyl, propen-2-yl, or buten-3-yl.

In another, more specific embodiment, this invention provides or contemplates a compound of formula A-I, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula A-II, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula A-II, where $R^O$ is isopropyl or sec-butyl.

In another, more specific embodiment, this invention provides or contemplates a compound of formula A-II, where $R^O$ is tert-butyl.

In another, more specific embodiment, this invention provides or contemplates a compound of formula A-II, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A-II, where $R^O$ is $C_2$-$C_8$ alkenyl, optionally substituted.

In another, more specific embodiment, this invention provides or contemplates a compound of formula A-II, where $R^O$ is $C_2$-$C_8$ alkynyl, optionally substituted.

In another, more specific embodiment, this invention provides or contemplates a compound of formula A-II, where $R^O$ is 2-propynyl, 3-butynyl, 2-butynyl, propen-2-yl, or buten-3-yl.

In another, more specific embodiment, this invention provides or contemplates a compound of formula A-II, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula A-III, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula A-III, where $R^O$ is isopropyl or sec-butyl.

In another, more specific embodiment, this invention provides or contemplates a compound of formula A-III, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A-III, where $R^O$ is $C_2$-$C_8$ alkenyl, optionally substituted.

In another, more specific embodiment, this invention provides or contemplates a compound of formula A-III, where $R^O$ is $C_2$-$C_8$ alkynyl, optionally substituted.

In another, more specific embodiment, this invention provides or contemplates a compound of formula A-III, where $R^O$ is 2-propynyl, 3-butynyl, 2-butynyl, propen-2-yl, or buten-3-yl.

In another, more specific embodiment, this invention provides or contemplates a compound of formula A-III, where $R^O$ is benzyl, o-chlorobenzyl, o-fluorobenzyl, o,o'-dichlorobenzyl, o,o'-difluorobenzyl.

In additional, more specific embodiments, this invention provides or contemplates compounds of formula A-II or formula A-III, and sub-generic embodiments thereof, as described in preceding paragraphs, where $R^a$ is in the para position.

In even more specific embodiments, this invention provides or contemplates compounds of formulas A-II and A-III, as described in several paragraphs above, where $R^a$ is p-fluoro, p-methyl, or p-trifluoromethyl.

In another, more specific embodiment, this invention provides or contemplates a compound of formula A-IV, where $R^O$ is a straight-chain $C_1$-$C_8$ alkyl group whose terminal methyl group is optionally substituted with one, two, or three Cl atoms or with one, two, or three F atoms.

In another, more specific embodiment, this invention provides or contemplates a compound of formula A-IV, where $R^O$ is isopropyl or sec-butyl.

In another, more specific embodiment, this invention provides or contemplates a compound of formula A-IV, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A-IV, where $R^O$ is $C_2$-$C_8$ alkenyl, optionally substituted.

In another, more specific embodiment, this invention provides or contemplates a compound of formula A-IV, where $R^O$ is $C_2$-$C_8$ alkynyl, optionally substituted.

In another, more specific embodiment, this invention provides or contemplates a compound of formula A-IV, where $R^O$ is 2-propynyl, 3-butynyl, 2-butynyl, propen-2-yl, or buten-3-yl.

In another, more specific embodiment, this invention provides or contemplates a compound of formula A-IV, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula A-V, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula A-V, where $R^O$ is isopropyl or sec-butyl.

In another, more specific embodiment, this invention provides or contemplates a compound of formula A-V, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A-V, where $R^O$ is $C_2$-$C_8$ alkenyl, optionally substituted.

In another, more specific embodiment, this invention provides or contemplates a compound of formula A-V, where $R^O$ is $C_2$-$C_8$ alkynyl, optionally substituted.

In another, more specific embodiment, this invention provides or contemplates a compound of formula A-V, where $R^O$ is 2-propynyl, 3-butynyl, 2-butynyl, propen-2-yl, or buten-3-yl.

In another, more specific embodiment, this invention provides or contemplates a compound of formula A-V, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula A-VI, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula A-VI, where $R^O$ is isopropyl or sec-butyl.

In another, more specific embodiment, this invention provides or contemplates a compound of formula A-VI, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula A-VI, where $R^O$ is $C_2$-$C_8$ alkenyl, optionally substituted.

In another, more specific embodiment, this invention provides or contemplates a compound of formula A-VI, where $R^O$ is $C_2$-$C_8$ alkynyl, optionally substituted.

In another, more specific embodiment, this invention provides or contemplates a compound of formula A-VI, where $R^O$ is 2-propynyl, 3-butynyl, 2-butynyl, propen-2-yl, or buten-3-yl.

In another, more specific embodiment, this invention provides or contemplates a compound of formula A-VI, where $R^O$ is benzyl, o-chlorobenzyl, o-fluorobenzyl, o,o'-dichlorobenzyl, or o,o'-difluorobenzyl.

In another, more specific embodiment, this invention provides or contemplates a compound of formula A, where $R^O$ is a straight-chain $C_1$-$C_8$ alkyl group whose terminal methyl group is optionally substituted with one, two, or three Cl atoms or one, two, or three F atoms, and where $R'''$ is H.

In another, more specific embodiment, this invention provides or contemplates a compound of formula A, where $R^O$ is isopropyl or sec-butyl, and where $R'''$ is H.

In another, more specific embodiment, this invention provides or contemplates a compound of formula A, where $R^O$ is ethyl, which is optionally substituted in the 2-position by methoxy or benzoyloxy; by one, two, or three fluorine atoms; or by one, two, or three chlorine atoms, and where $R'''$ is H.

In another, more specific embodiment, this invention provides or contemplates a compound of formula A, where $R^O$ is $C_2$-$C_8$ alkenyl, optionally substituted, and where $R'''$ is H.

In another, more specific embodiment, this invention provides or contemplates a compound of formula A, where $R^O$ is $C_2$-$C_8$ alkynyl, optionally substituted, and where $R^{'m}$ is H.

In another, more specific embodiment, this invention provides or contemplates a compound of formula A, where $R^O$ is 2-propynyl, 3-butynyl, 2-butynyl, propen-2-yl, or buten-3-yl, and where $R^{'m}$ is H.

In another, more specific embodiment, this invention provides or contemplates a compound of formula A, where $R^O$ is benzyl, o-chlorobenzyl, o-fluorobenzyl, o,o'-dichlorobenzyl, o,o'-difluorobenzyl.

In another embodiment, this invention provides or contemplates a composition comprising a pharmaceutically acceptable carrier and one of more of the following: a compound of formula A and a salt, ester, or prodrug thereof.

In another embodiment, this invention provides or contemplates a composition comprising a pharmaceutically acceptable carrier and one of more of the following: a compound of formula B and a salt, ester, or prodrug thereof.

In another embodiment, this invention contemplates a method of treating a disease or disorder which is affected by activation of potassium ion channels comprising administering to a patient in need thereof a therapeutically affective amount of a composition comprising one of more of the following: a compound of formula A and a salt, ester, or prodrug thereof.

In another embodiment, this invention contemplates a method of treating a disease or disorder which is affected by activation of potassium ion channels comprising administering to a patient in need thereof a therapeutically affective amount of a composition comprising one of more of the following: a compound of formula B and a salt, ester, or prodrug thereof.

In another embodiment, this invention contemplates a method of diagnosing a disease or disorder which is affected by activation of potassium ion channels comprising administering to a patient suspected of having such disease or disorder a probe comprising an isotopically labeled compound of formula A and/or a salt, ester, or prodrug thereof; monitoring the binding of that compound by radiological methods; and correlating such binding to other characteristics of the disease or disorder.

In another embodiment, this invention contemplates a method of diagnosing a disease or disorder which is affected by activation of potassium ion channels comprising administering to a patient suspected of having such disease or disorder a probe comprising an isotopically labeled compound of formula B and/or a salt, ester, or prodrug thereof; monitoring the binding of that compound by radiological methods; and correlating such binding to other characteristics of the disease or disorder.

In one subgeneric embodiment, this invention provides a compound of formula B-I below

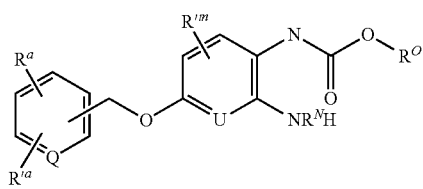

where Q is —CH= or —N=.

In a more specific subgeneric embodiment, this invention provides a compound of formula B-I in which $R^{'m}$ is H.

In another more specific subgeneric embodiment the invention provides compounds of formula B-II.

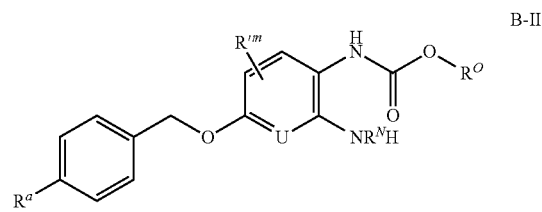

In a still more specific subgeneric embodiment, this invention provides a compound of formula B-II in which $R^{'m}$ is H.

In another still more specific subgeneric embodiment, this invention provides a compound of formula B-II in which $R^{'m}$ is Cl or F.

In another still more specific subgeneric embodiment, this invention provides or contemplates a compound of formula B-II where U is —C($R^m$)=.

In another still more specific subgeneric embodiment, this invention provides or contemplates a compound of formula B-II where U is —CH=.

In another more specific subgeneric embodiment, this invention provides or contemplates a compound of formula B-II where U is —N=.

In another subgeneric embodiment, the invention provides a compound of formula B-III,

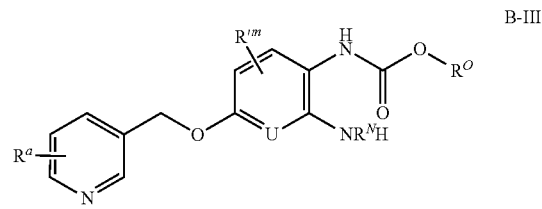

In one more specific subgeneric embodiment, this invention provides or contemplates a compound of formula B-III where U is —C($R^m$)=.

In another still more specific subgeneric embodiment, this invention provides a compound of formula B-III in which $R^{'m}$ is H.

In another more specific subgeneric embodiment, this invention provides or contemplates a compound of formula B-III where U is —N=.

In another subgeneric embodiment, the invention provides a compound of formula B-IV,

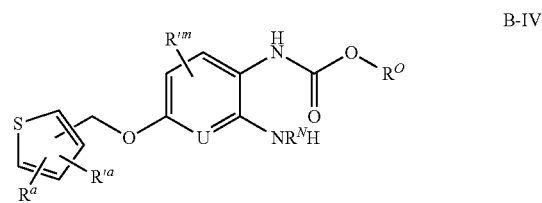

In one more specific subgeneric embodiment, this invention provides or contemplates a compound of formula B-IV where U is —C($R^m$)=.

In another still more specific subgeneric embodiment, this invention provides a compound of formula B-IV in which $R^{'m}$ is H.

In another more specific subgeneric embodiment, this invention provides or contemplates a compound of formula B-IV where U is —N=.

In another subgeneric embodiment, the invention provides a compound of formula B-V,

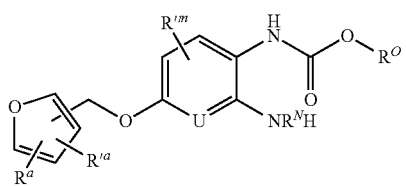

B-V

In one more specific subgeneric embodiment, this invention provides or contemplates a compound of formula B-V where U is —C($R'''$)=.

In another still more specific subgeneric embodiment, this invention provides a compound of formula B-V in which $R'''$ is H.

In another more specific subgeneric embodiment, this invention provides or contemplates a compound of formula B-V where U is —N=.

In another subgeneric embodiment, the invention provides a compound of formula B-VI,

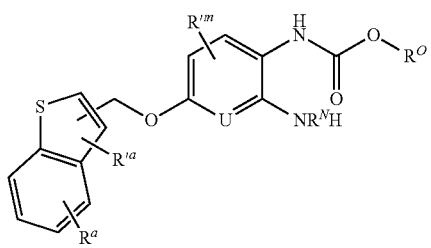

B-VI

In one more specific subgeneric embodiment, this invention provides or contemplates a compound of formula B-VI where U is —C($R'''$)=.

In another still more specific subgeneric embodiment, this invention provides a compound of formula B-VI in which $R'''$ is H.

In another more specific subgeneric embodiment, this invention provides or contemplates a compound of formula B-VI where $R'''$ is H and U is —N=.

In another, more specific embodiment, this invention provides or contemplates a compound of formula B, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula B, where $R^O$ is isopropyl or sec-butyl.

In another, more specific embodiment, this invention provides or contemplates a compound of formula B, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B, where $R^O$ is $C_2$-$C_8$ alkenyl, optionally substituted.

In another, more specific embodiment, this invention provides or contemplates a compound of formula B, where $R^O$ is isobutyl or tert-butyl.

In another, more specific embodiment, this invention provides or contemplates a compound of formula B, where $R^O$ is $C_2$-$C_8$ alkynyl, optionally substituted.

In another, more specific embodiment, this invention provides or contemplates a compound of formula B, where $R^O$ is 2-propynyl, 3-butynyl, 2-butynyl, propen-2-yl, or buten-3-yl.

In another, more specific embodiment, this invention provides or contemplates a compound of formula B, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula B-I, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula B-I, where $R^O$ is isopropyl or sec-butyl.

In another, more specific embodiment, this invention provides or contemplates a compound of formula B-I, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B-I, where $R^O$ is $C_2$-$C_8$ alkenyl, optionally substituted.

In another, more specific embodiment, this invention provides or contemplates a compound of formula B-I, where $R^O$ is $C_2$-$C_8$ alkynyl, optionally substituted.

In another, more specific embodiment, this invention provides or contemplates a compound of formula B-I, where $R^O$ is 2-propynyl, 3-butynyl, 2-butynyl, propen-2-yl, or buten-3-yl.

In another, more specific embodiment, this invention provides or contemplates a compound of formula B-I, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula B-II, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula B-II, where $R^O$ is isopropyl or sec-butyl.

In another, more specific embodiment, this invention provides or contemplates a compound of formula B-II, where $R^O$ is tert-butyl.

In another, more specific embodiment, this invention provides or contemplates a compound of formula B-II, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B-II, where $R^O$ is $C_2$-$C_8$ alkenyl, optionally substituted.

In another, more specific embodiment, this invention provides or contemplates a compound of formula B-II, where $R^O$ is $C_2$-$C_8$ alkynyl, optionally substituted.

In another, more specific embodiment, this invention provides or contemplates a compound of formula B-II, where $R^O$ is 2-propynyl, 3-butynyl, 2-butynyl, propen-2-yl, or buten-3-yl.

In another, more specific embodiment, this invention provides or contemplates a compound of formula B-II, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula B-III, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula B-III, where $R^O$ is isopropyl or sec-butyl.

In another, more specific embodiment, this invention provides or contemplates a compound of formula B-III, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B-III, where $R^O$ is $C_2$-$C_8$ alkenyl, optionally substituted.

In another, more specific embodiment, this invention provides or contemplates a compound of formula B-III, where $R^O$ is $C_2$-$C_8$ alkynyl, optionally substituted.

In another, more specific embodiment, this invention provides or contemplates a compound of formula B-III, where $R^O$ is 2-propynyl, 3-butynyl, 2-butynyl, propen-2-yl, or buten-3-yl.

In another, more specific embodiment, this invention provides or contemplates a compound of formula B-III, where $R^O$ is benzyl, o-chlorobenzyl, o-fluorobenzyl, o,o'-dichlorobenzyl, o,o'-difluorobenzyl.

In additional, more specific embodiments, this invention provides or contemplates compounds of formula B-II or formula B-III, and sub-generic embodiments thereof, as described in preceding paragraphs, where $R^a$ is in the para position.

In even more specific embodiments, this invention provides or contemplates compounds of formulas B-II and B-III, as described in several paragraphs above, where $R^a$ is p-fluoro, p-methyl, or p-trifluoromethyl.

In another, more specific embodiment, this invention provides or contemplates a compound of formula B-IV, where $R^O$ is a straight-chain $C_1$-$C_8$ alkyl group whose terminal methyl group is optionally substituted with one, two, or three Cl atoms or with one, two, or three F atoms.

In another, more specific embodiment, this invention provides or contemplates a compound of formula B-IV, where $R^O$ is isopropyl or sec-butyl.

In another, more specific embodiment, this invention provides or contemplates a compound of formula B-IV, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B-IV, where $R^O$ is $C_2$-$C_8$ alkenyl, optionally substituted.

In another, more specific embodiment, this invention provides or contemplates a compound of formula B-IV, where $R^O$ is $C_2$-$C_8$ alkynyl, optionally substituted.

In another, more specific embodiment, this invention provides or contemplates a compound of formula B-IV, where $R^O$ is 2-propynyl, 3-butynyl, 2-butynyl, propen-2-yl, or buten-3-yl.

In another, more specific embodiment, this invention provides or contemplates a compound of formula B-IV, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula B-V, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula B-V, where $R^O$ is isopropyl or sec-butyl.

In another, more specific embodiment, this invention provides or contemplates a compound of formula B-V, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B-V, where $R^O$ is $C_2$-$C_8$ alkenyl, optionally substituted.

In another, more specific embodiment, this invention provides or contemplates a compound of formula B-V, where $R^O$ is $C_2$-$C_8$ alkynyl, optionally substituted.

In another, more specific embodiment, this invention provides or contemplates a compound of formula B-V, where $R^O$ is 2-propynyl, 3-butynyl, 2-butynyl, propen-2-yl, or buten-3-yl.

In another, more specific embodiment, this invention provides or contemplates a compound of formula B-V, where $R^O$ is benzyl, o-chlorobenzyl, o-fluorobenzyl, o,o'-dichlorobenzyl, o,o'-difluorobenzyl.

In another, more specific embodiment, this invention provides or contemplates a compound of formula B-VI, where $R^O$ is a straight-chain $C_1$-$C_8$ alkyl group whose terminal methyl group is optionally substituted with one, two, or three Cl atoms or one, two, or three F atoms.

In another, more specific embodiment, this invention provides or contemplates a compound of formula B-VI, where $R^O$ is isopropyl or sec-butyl.

In another, more specific embodiment, this invention provides or contemplates a compound of formula B-VI, where $R^O$ is ethyl, which is optionally substituted in the 2-position by methoxy or benzoyloxy; by one, two, or three fluorine atoms; or by one, two, or three chlorine atoms.

In another, more specific embodiment, this invention provides or contemplates a compound of formula B-VI, where $R^O$ is $C_2$-$C_8$ alkenyl, optionally substituted.

In another, more specific embodiment, this invention provides or contemplates a compound of formula B-VI, where $R^O$ is $C_2$-$C_8$ alkynyl, optionally substituted.

In another, more specific embodiment, this invention provides or contemplates a compound of formula B-VI, where $R^O$ is 2-propynyl, 3-butynyl, 2-butynyl, propen-2-yl, or buten-3-yl.

In another, more specific embodiment, this invention provides or contemplates a compound of formula B-VI, where $R^O$ is benzyl, o-chlorobenzyl, o-fluorobenzyl, o,o'-dichlorobenzyl, or o,o'-difluorobenzyl.

In another, more specific embodiment, this invention provides or contemplates a compound of formula B, where $R^O$ is a straight-chain $C_1$-$C_8$ alkyl group whose terminal methyl group is optionally substituted with one, two, or three Cl atoms or one, two, or three F atoms, and where $R^{\prime m}$ is H, methyl, or F.

In another, more specific embodiment, this invention provides or contemplates a compound of formula B, where $R^O$ is isopropyl or sec-butyl, and where $R^{\prime m}$ is H, methyl, or F.

In another, more specific embodiment, this invention provides or contemplates a compound of formula B, where $R^O$ is ethyl, which is optionally substituted in the 2-position by methoxy or benzoyloxy; by one, two, or three fluorine atoms; or by one, two, or three chlorine atoms, and where R'''' is H, methyl, or F.

In another, more specific embodiment, this invention provides or contemplates a compound of formula B, where $R^O$ is $C_2$-$C_8$ alkenyl, optionally substituted, and where R'''' is H, methyl, or F.

In another, more specific embodiment, this invention provides or contemplates a compound of formula B, where $R^O$ is $C_2$-$C_8$ alkynyl, optionally substituted, and where R'''' is H, methyl, or F.

In another, more specific embodiment, this invention provides or contemplates a compound of formula B, where $R^O$ is 2-propynyl, 3-butynyl, 2-butynyl, propen-2-yl, or buten-3-yl, and where R'''' is H, methyl, or F.

In another, more specific embodiment, this invention provides or contemplates a compound of formula B, where $R^O$ is benzyl, o-chlorobenzyl, o-fluorobenzyl, o,o'-dichlorobenzyl, o,o'-difluorobenzyl, and where R'''' is H, methyl, or F.

In yet more specific embodiments, this invention provides or contemplates compounds of formulas A, A-I, A-II, A-III, A-IV, A-V, and A-VI, and sub-embodiments thereof, as described in the preceding paragraphs, where $R^N$ is H, methyl, or ethyl.

In even more specific embodiments, this invention provides or contemplates compounds of formulas A, A-I, A-II, A-III, A-IV, A-V, and A-VI, and sub-embodiments thereof, as described in the preceding paragraphs, where $R^N$ is H, methyl, or ethyl and R'''' is H, F, Cl, or methyl.

In additional even more specific embodiments, this invention provides or contemplates compounds of formulas A, A, A-I, A-II, A-III, A-IV, A-V, and A-VI, and sub-embodiments thereof, as described in the preceding paragraphs, where $R^N$ is H or methyl and R'''' is F or Cl.

In additional even more specific embodiments, this invention provides or contemplates compounds of formulas A, A-I, A-II, A-III, A-IV, A-V, and A-VI, and sub-embodiments thereof, as described in the preceding paragraphs, where $R^N$ is H or methyl and R'''' is halomethyl or methoxy.

In other more specific embodiments, this invention provides or contemplates compounds of formulas A, A-I, A-II, A-III, A-IV, A-V, and A-VI, and sub-SDO embodiments thereof, as described in the preceding paragraphs, where $R^N$ is H or methyl and R'''' is ortho to the amide group.

In yet more specific embodiments, this invention provides or contemplates compounds of formulas A, A-I, A-II, A-III, A-IV, A-V, and A-VI, and sub-embodiments thereof, as described in the preceding paragraphs, where $R^N$ is H or methyl and R'''' is meta to the amide group.

In additional more specific embodiments, this invention provides or contemplates compounds of formulas A, A-I, A-II, A-III, A-IV, A-V, and A-VI, and sub-embodiments thereof, as described in the preceding paragraphs, where $R^N$ is H or methyl and R'''' is ortho to the carbamate group and is methoxy, methyl, or halomethyl.

In yet more specific embodiments, this invention provides or contemplates compounds of formulas A, A-I, A-II, A-III, A-IV, A-V, and A-VI, and sub-embodiments thereof, as described in the preceding paragraphs, where $R^N$ is H or methyl and R'''' is meta to the carbamate group and is halogen, methyl, or halomethyl.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H, methyl, or ethyl.

In even more specific embodiments, this invention provides or contemplates compounds of formulas B, B-I, B-II, B-III, B-IV, B-V, and B-VI, and sub-embodiments thereof, as described in the preceding paragraphs, where $R^N$ is H, methyl, or ethyl and R'''' is H or methyl.

In additional even more specific embodiments, this invention provides or contemplates compounds of formulas B, B-I, B-II, B-III, B-IV, B-V, and B-VI, and sub-embodiments thereof, as described in the preceding paragraphs, where $R^N$ is H, methyl, or ethyl and R'''' is methoxy, F, or Cl.

In additional even more specific embodiments, this invention provides or contemplates compounds of formulas B, B-I, B-II, B-III, B-IV, B-V, and B-VI, and sub-embodiments thereof, as described in the preceding paragraphs, where $R^N$ is H, methyl, or ethyl and R'''' is halomethyl or methoxy.

In other more specific embodiments, this invention provides or contemplates compounds of formulas B, B-I, B-II, B-III, B-IV, B-V, and B-VI, and sub-embodiments thereof, as described in the preceding paragraphs, where $R^N$ is H or methyl and R'''' is ortho to the carbamate group.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H or methyl and R'''' is meta to the carbamate group.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H or methyl and R'''' is ortho to the carbamate group and is methoxy, methyl, or halomethyl.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H or methyl and R'''' is meta to the carbamate group and is halogen, methyl, or halomethyl.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H or methyl and R'''' is ortho to the carbamate group and is fluoromethyl.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H or methyl and R'''' is meta to the carbamate group and is fluoromethyl.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H and R'''' is ortho to the carbamate group and is trifluoromethyl.

In yet more specific embodiments, this invention provides or contemplates compounds of formulas B, B-I, B-II, B-III, B-IV, B-V, and B-VI, and sub-embodiments thereof, as described in the preceding paragraphs, where $R^N$ is H and R'''' is meta to the carbamate group and is trifluoromethyl.

In another embodiment, this invention provides or contemplates a composition comprising a pharmaceutically acceptable carrier and one of more of the following: a compound of formula B and a salt, ester or prodrug thereof.

In another embodiment, this invention contemplates a method of treating a disease or disorder which is affected by activation of potassium ion channels comprising administering to a patient in need thereof a therapeutically affective amount of a composition comprising one of more of the following: a compound of formula B and a salt, ester or prodrug thereof.

In another embodiment, this invention contemplates a method of diagnosing a disease or disorder which is affected by activation of potassium ion channels comprising administering to a patient suspected of having such disease or disorder a probe comprising an isotopically labeled compound of formula B and/or a salt, ester or prodrug thereof; monitoring the binding of that compound by radiological methods; and correlating such binding to other characteristics of the disease or disorder.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tabletting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

For oral administration, the pharmaceutical compositions may take the form of, for example, tablets or capsules prepared by conventional means with pharmaceutically acceptable excipients such as binders, fillers, lubricants, disintegrating agents, and wetting agents. The tablets may be coated by standard pharmaceutical methods. Liquid preparations for oral administration may take the form of solutions, syrups or suspensions, among many variations, or they may be presented as a dry product for constitution with water or other suitable vehicle before use. Such liquid preparations may be prepared by conventional means with pharmaceutically acceptable additives such as suspending agents (e.g., syrups and edible fats); emulsifying agents (e.g., lecithin or acacia); non-aqueous vehicles (e.g., almond oil or ethyl alcohol); and preservatives (e.g., sorbic acid or various p-hydroxybenzoates).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules, or in multi-dose containers, with an added preservative. The compositions may take such forms as suspensions, solutions, or emulsions in oily or aqueous vehicles, and may contain formulating agents such as suspending, stabilizing and dispersing agents.

DETAILED DESCRIPTION

As used herein, the term alkyl, if not otherwise qualified denotes a either a straight-chain or a branched moiety. As used herein, all generic and specific chemical formulas include all tautomeric forms and all isotopically labeled forms.

Prophetic Examples

The prophetic examples shown below are provided to illustrate by means of examples the scope of this invention. This set of examples should not be construed as limiting this invention.

One group of prophetic examples of compounds of formula A comprises compounds of the formula below

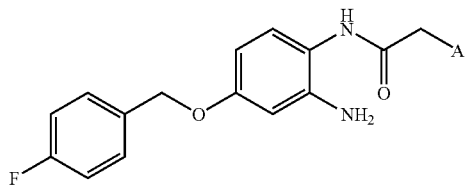

where A is selected from: H; $CH_3$; $CH_2CH_3$; $CH_2OCH_3$; $(CH_2)_2CH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2(o\text{-}Cl\text{---}C_6H_4)$.

Another group of prophetic examples comprises compounds of the formula below

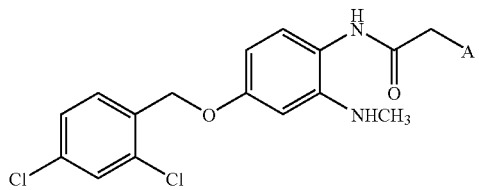

where A is selected from: H; $CH_3$; $CH_2CH_3$; $(CH_2)_2CH_3$; $CH_2OCH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2OCH_2\text{---}(m\text{-}F\text{---}C_6H_4)$; $CH_2(o\text{-}Cl\text{---}C_6H_4)$.

Another group of prophetic examples comprises compounds of the formula below

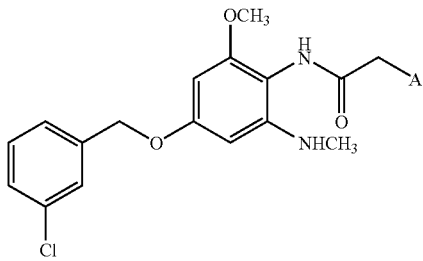

where A is selected from: H; CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$— (m-F—C$_6$H$_4$); CH$_2$(o-Cl—C$_6$H$_4$).

Another group of prophetic examples comprises compounds of the formula below

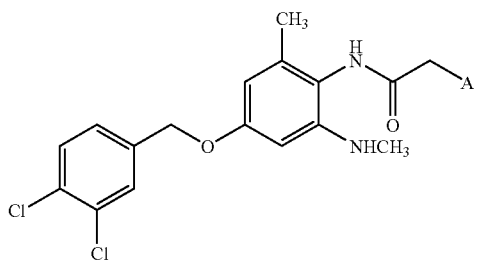

where A is selected from: H; CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$— (m-F—C$_6$H$_4$); CH$_2$(o-Cl—C$_6$H$_4$).

Another group of prophetic examples comprises compounds of the formula below

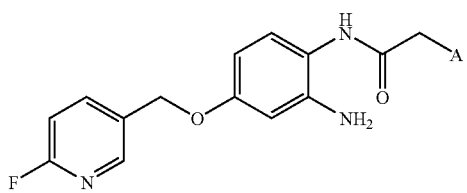

where A is selected from: H; CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$(o-Cl—C$_6$H$_4$).

Yet another group of prophetic examples comprises compounds of the formula below

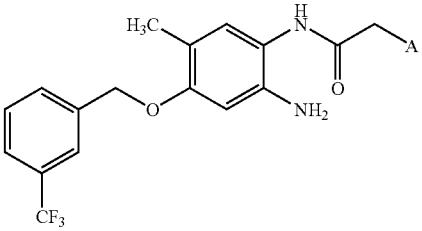

where A is selected from: CH$_3$; CH$_2$CH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$— (m-F—C$_6$H$_4$); CH$_2$(o-Cl—C$_6$H$_4$).

Yet another group of prophetic examples comprises compounds of the formula below

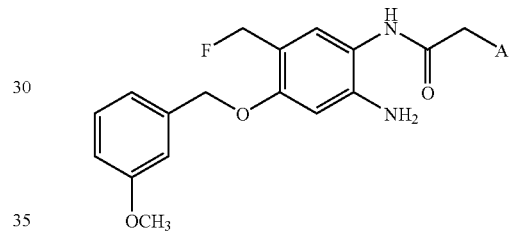

where A is selected from: H; CH$_3$; CH$_2$CH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Yet another group of prophetic examples comprises compounds of the formula below

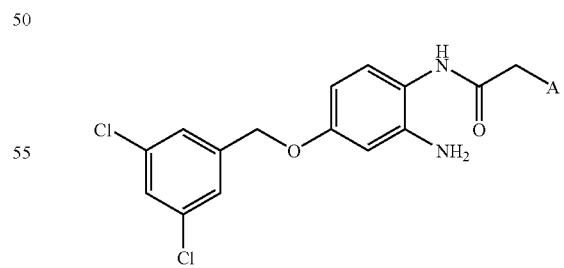

where A is selected from: H; CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Yet another group of prophetic examples comprises compounds of the formula below

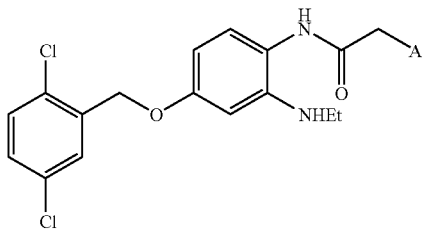

where A is selected from: H; CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Yet another group of prophetic examples comprises compounds of the formula below

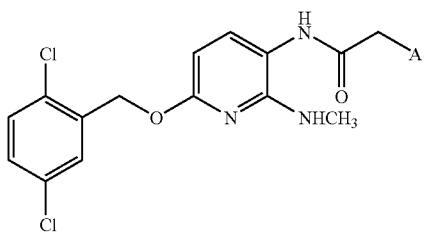

where A is selected from: H; CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH=CH$_2$; CH$_2$CH$_2$OCH$_3$; CH$_2$CH$_2$C≡CH; CH$_2$CH=CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Additional examples are presented in the tables below:

| V | U | R$^N$ | R$^O$ |
|---|---|---|---|
| 4-F-pyridin-3-yl | —CH= | H | —CH$_2$CH$_3$ |
| 4-F-pyridin-3-yl | —CH= | H | —(CH$_2$)$_2$(CH$_3$)$_2$ |
| 4-F-pyridin-3-yl | —CH= | H | —CH$_2$CH$_2$F |
| 4-F-pyridin-3-yl | —CH= | H | —(CH$_2$)$_3$CH$_3$ |
| 4-F-pyridin-3-yl | —CH= | H | (CH$_2$)$_4$CH$_3$ |
| 4-F-pyridin-3-yl | —CH= | H | Benzyloxyethyl- |
| 4-F-pyridin-3-yl | —CH= | H | 2-Cl-benzyl- |
| 4-F-phenyl | —N= | H | —CH$_2$CH$_3$ |
| 4-F-phenyl | —N= | H | —(CH$_2$)$_2$(CH$_3$)$_2$ |
| 4-F-phenyl | —N= | H | —CH$_2$CH$_2$F |
| 4-F-phenyl | —N= | H | —(CH$_2$)$_3$CH$_3$ |
| 4-F-phenyl | —N= | H | (CH$_2$)$_4$CH$_3$ |
| 4-F-phenyl | —N= | H | Benzyloxyethyl- |
| 4-F-phenyl | —N= | H | 2-Cl-benzyl- |
| 4-F-phenyl | —CH= | —CH$_3$ | —CH$_2$CH$_3$ |
| 4-F-phenyl | —CH= | —CH$_3$ | —(CH$_2$)$_2$(CH$_3$)$_2$ |
| 4-F-phenyl | —CH= | —CH$_3$ | —CH$_2$CH$_2$F |
| 4-F-phenyl | —CH= | —CH$_3$ | —(CH$_2$)$_3$CH$_3$ |
| 4-F-phenyl | —CH= | —CH$_3$ | (CH$_2$)$_4$CH$_3$ |

| V | U | R$^N$ | R$^O$ |
|---|---|---|---|
| 4-F-phenyl | —CH= | —CH$_3$ | Benzyloxyethyl- |
| 4-F-phenyl | —CH= | —CH$_3$ | 2-Cl-benzyl- |
| 4-F-phenyl | —N= | —CH$_3$ | —CH$_2$CH$_3$ |
| 4-F-phenyl | —N= | —CH$_3$ | —(CH$_2$)$_2$(CH$_3$)$_2$ |
| 4-F-phenyl | —N= | —CH$_3$ | —CH$_2$CH$_2$F |
| 4-F-phenyl | —N= | —CH$_3$ | —(CH$_2$)$_3$CH$_3$ |
| 4-F-phenyl | —N= | —CH$_3$ | (CH$_2$)$_4$CH$_3$ |
| 4-F-phenyl | —N= | —CH$_3$ | Benzyloxyethyl- |
| 4-F-phenyl | —N= | —CH$_3$ | 2-Cl-benzyl- |

Additional prophetic examples are given in the following tables:

| Q | R$^3$ | R$^4$ | R$^5$ |
|---|---|---|---|
| S | H | H | H |
| S | CH$_3$ | H | H |
| S | H | H | CH$_3$ |
| S | H | H | Cl |
| S | Cl | H | H |
| S | OMe | Br | H |
| S | H | H | C$_6$H$_5$ |
| S | Br | H | H |
| S | H | Br | H |
| S | H | H | F |
| S | H | H | CH$_2$CH$_3$ |
| O | H | H | H |
| O | CH$_3$ | H | H |
| O | H | H | CH$_3$ |
| O | H | H | Cl |
| O | Cl | H | H |
| O | OMe | Br | H |
| O | H | H | C$_6$H$_5$ |
| O | Br | H | H |
| O | H | Br | H |
| O | H | H | F |
| O | H | H | CH$_2$CH$_3$ |

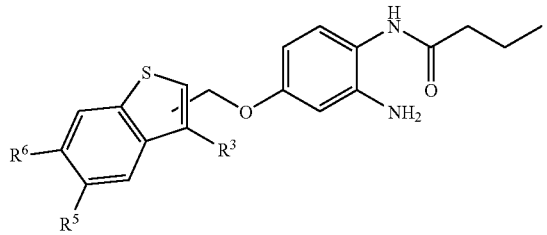

| $R^3$ | Benzothien- | $R^5$ | $R^6$ |
| --- | --- | --- | --- |
| H | 2-yl | H | H |
| H | 2-yl | H | H |
| NONE | 3-yl | F | H |
| $CH_3$ | 2-yl | $N(CH_3)_2$ | H |
| NONE | 3-yl | $N(CH_3)_2$ | H |
| $OCH_3$ | 2-yl | H | Cl |

One group of prophetic examples for compounds of formula B comprises compounds of the formula below

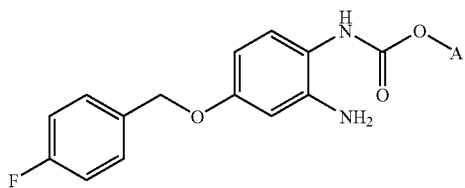

where A is selected from: $CH_3$; $CH_2CH_3$; $CH_2OCH_3$; $(CH_2)_2CH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2(o\text{-}Cl\text{-}C_6H_4)$.

Another group of prophetic examples comprises compounds of the formula below

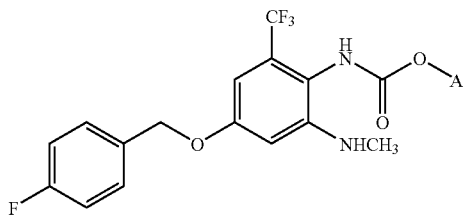

where A is selected from: $CH_3$; $CH_2CH_3$; $(CH_2)_2CH_3$; $CH_2OCH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2OCH_2$—$(m\text{-}F\text{-}C_6H_4)$; $CH_2(o\text{-}Cl\text{-}C_6H_4)$.

Another group of prophetic examples comprises compounds of the formula below

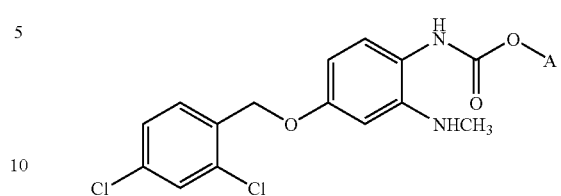

where A is selected from: $CH_3$; $CH_2CH_3$; $CH_2OCH_3$; $(CH_2)_2CH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2OCH_2$—$(m\text{-}F\text{-}C_6H_4)$; $CH_2(o\text{-}Cl\text{-}C_6H_4)$.

Another group of prophetic examples comprises compounds of the formula below

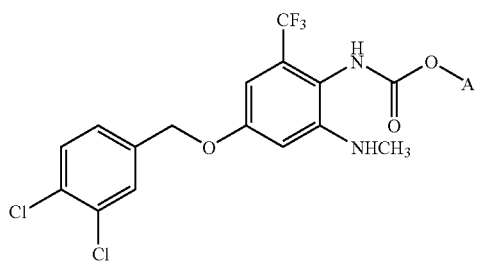

where A is selected from: $CH_3$; $CH_2CH_3$; $CH_2OCH_3$; $(CH_2)_2CH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2OCH_2$—$(m\text{-}F\text{-}C_6H_4)$; $CH_2(o\text{-}Cl\text{-}C_6H_4)$.

Another group of prophetic examples comprises compounds of the formula below

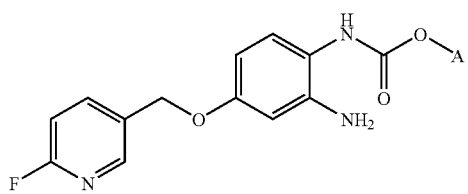

where A is selected from: $CH_3$; $CH_2CH_3$; $CH_2OCH_3$; $(CH_2)_2CH_3$; $CH(CH_3)_2$; $CH_2C\equiv CH$; $CH_2CH_2F$; $CH_2CH=CH_2$; $CH_2CH_2OCH_3$; $CH_2CH_2C\equiv CH$; $CH_2CH=CH_2$; $CH_2C\equiv CCH_3$; $CH_2C(CH_3)_3$; $(CH_2)_7CH_3$; $CH_2OCH_2C_6H_5$; $CH_2(o\text{-}Cl\text{-}C_6H_4)$.

Yet another group of prophetic examples comprises compounds of the formula below

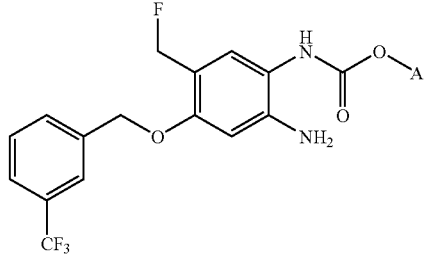

where A is selected from: CH$_3$; CH$_2$CH$_3$; (CH$_2$)$_2$CH$_3$; CH(CH$_3$)$_2$; CH$_2$C≡CH; CH$_2$CH$_2$F; CH$_2$CH═CH$_2$; CH$_2$CH$_2$OCH$_3$; CH$_2$CH$_2$C≡CH; CH$_2$CH═CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$— (m-F—C$_6$H$_4$); CH$_2$(o-Cl—C$_6$H$_4$).

Yet another group of prophetic examples comprises compounds of the formula below

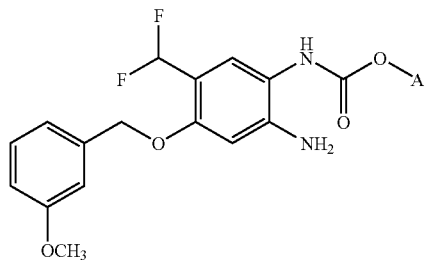

where A is selected from: CH$_3$; CH$_2$CH$_3$; (CH$_2$)$_2$CH$_3$; CH(CH$_3$)$_2$; CH$_2$C≡CH; CH$_2$CH$_2$F; CH$_2$CH═CH$_2$; CH$_2$CH$_2$OCH$_3$; CH$_2$CH$_2$C≡CH; CH$_2$CH═CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Yet another group of prophetic examples comprises compounds of the formula below

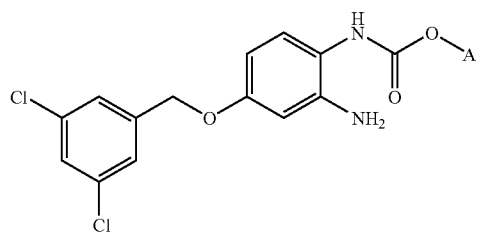

where A is selected from: CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH═CH$_2$; CH$_2$CH$_2$OCH$_3$; CH$_2$CH$_2$C≡CH; CH$_2$CH═CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Yet another group of prophetic examples comprises compounds of the formula below

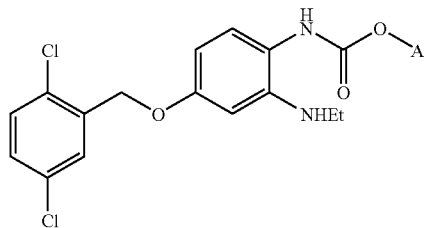

where A is selected from: CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH═CH$_2$; CH$_2$CH$_2$OCH$_3$; CH$_2$CH$_2$C≡CH; CH$_2$CH═CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Yet another group of prophetic examples comprises compounds of the formula below

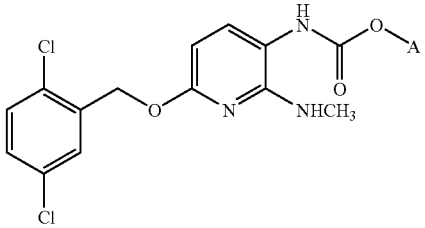

where A is selected from: CH$_3$; CH$_2$CH$_3$; CH$_2$OCH$_3$; (CH$_2$)$_2$CH$_3$; CH(CH$_3$)$_2$; CH$_2$C≡CH; CH$_2$CH$_2$F; CH$_2$CH═CH$_2$; CH$_2$CH$_2$OCH$_3$; CH$_2$CH$_2$C≡CH; CH$_2$CH═CH$_2$; CH$_2$C≡CCH$_3$; CH$_2$C(CH$_3$)$_3$; (CH$_2$)$_7$CH$_3$; CH$_2$OCH$_2$C$_6$H$_5$; CH$_2$OCH$_2$ (m-F—C$_6$H$_4$); CH$_2$(o-Cl—C$_6$H$_4$).

Additional prophetic examples are presented in the tables below:

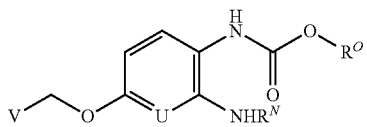

| V | U | R$^N$ | R$^O$ |
|---|---|---|---|
| 4-F-pyridin-3-yl | —CH═ | H | —CH$_2$CH$_3$ |
| 4-F-pyridin-3-yl | —CH═ | H | —(CH$_2$)$_2$(CH$_3$)$_2$ |
| 4-F-pyridin-3-yl | —CH═ | H | —CH$_2$CH$_2$F |
| 4-F-pyridin-3-yl | —CH═ | H | —(CH$_2$)$_3$CH$_3$ |
| 4-F-pyridin-3-yl | —CH═ | H | (CH$_2$)$_4$CH$_3$ |
| 4-F-pyridin-3-yl | —CH═ | H | Benzyloxyethyl- |
| 4-F-pyridin-3-yl | —CH═ | H | 2-Cl-benzyl- |
| 4-F-phenyl | —N═ | H | —CH$_2$CH$_3$ |
| 4-F-phenyl | —N═ | H | —(CH$_2$)$_2$(CH$_3$)$_2$ |
| 4-F-phenyl | —N═ | H | —CH$_2$CFH$_2$ |
| 4-F-phenyl | —N═ | H | —(CH$_2$)$_3$CH3 |
| 4-F-phenyl | —N═ | H | (CH$_2$)$_4$CH$_3$ |
| 4-F-phenyl | —N═ | H | Benzyloxyethyl- |
| 4-F-phenyl | —N═ | H | 2-Cl-benzyl- |
| 4-F-phenyl | —CH═ | —CH$_3$ | —CH$_2$CH$_3$ |
| 4-F-phenyl | —CH═ | —CH$_3$ | —(CH$_2$)$_2$(CH$_3$)$_2$ |
| 4-F-phenyl | —CH═ | —CH$_3$ | —CH$_2$CFH$_2$ |
| 4-F-phenyl | —CH═ | —CH$_3$ | —(CH$_2$)$_3$CH$_3$ |
| 4-F-phenyl | —CH═ | —CH$_3$ | (CH$_2$)$_4$CH$_3$ |
| 4-F-phenyl | —CH═ | —CH$_3$ | Benzyloxyethyl- |
| 4-F-phenyl | —CH═ | —CH$_3$ | 2-Cl-benzyl- |
| 4-F-phenyl | —N═ | —CH$_3$ | —CH$_2$CH$_3$ |
| 4-F-phenyl | —N═ | —CH$_3$ | —(CH$_2$)$_2$(CH$_3$)$_2$ |
| 4-F-phenyl | —N═ | —CH$_3$ | —CH$_2$CFH2 |
| 4-F-phenyl | —N═ | —CH$_3$ | —(CH$_2$)$_3$CH$_3$ |
| 4-F-phenyl | —N═ | —CH$_3$ | (CH$_2$)$_4$CH$_3$ |
| 4-F-phenyl | —N═ | —CH$_3$ | Benzyloxyethyl- |
| 4-F-phenyl | —N═ | —CH$_3$ | 2-Cl-benzyl- |

Additional prophetic examples are given in the following tables:

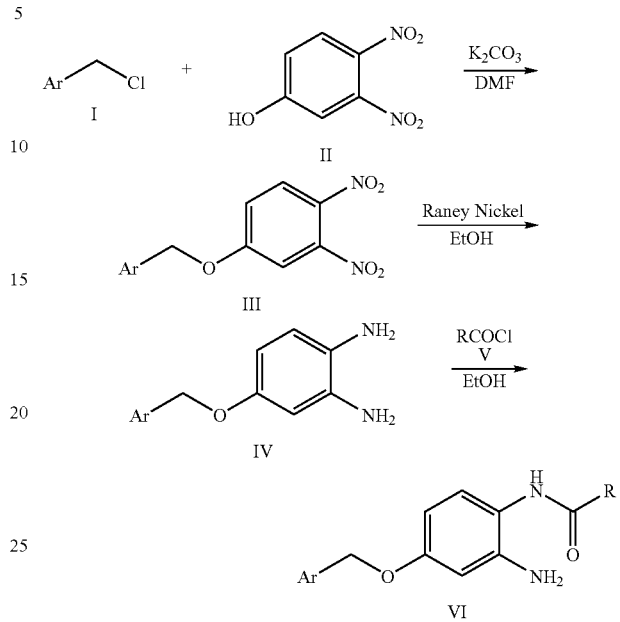

| Q | R³ | R⁴ | R⁵ |
|---|----|----|----|
| S | H | H | H |
| S | CH₃ | H | H |
| S | H | H | CH₃ |
| S | H | H | Cl |
| S | Cl | H | H |
| S | OMe | Br | H |
| S | H | H | C₆H₅ |
| S | Br | H | H |
| S | H | Br | H |
| S | H | H | F |
| S | H | H | CH₂CH₃ |
| O | H | H | H |
| O | CH₃ | H | H |
| O | H | H | CH₃ |
| O | H | H | Cl |
| O | Cl | H | H |
| O | OMe | Br | H |
| O | H | H | C₆H₅ |
| O | Br | H | H |
| O | H | Br | H |
| O | H | H | F |
| O | H | H | CH₂CH₃ |

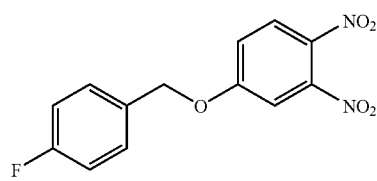 [SMILES: O=[N+]([O-])c1ccc(OCc2ccc(F)cc2)cc1[N+](=O)[O-]]

| R³ | Benzothien- | Rᵐ | R⁵ | R⁶ |
|----|-------------|-----|----|----|
| H | 3-yl | CH₃ | H | H |
| H | 3-yl | CF₃ | H | H |
| H | 2-yl | CF₃ | H | H |
| H | 2-yl | CH₃ | H | H |
| H | 3-yl | H | F | F |
| H | 2-yl | H | H | H |
| H | 2-yl | H | H | H |
| H | 3-yl | H | F | H |
| CH₃ | 2-yl | H | N(CH₃)₂ | H |
| H | 3-yl | H | N(CH₃)₂ | H |
| OCH₃ | 2-yl | H | H | Cl |

Synthetic Schemes

The compounds of the invention can be synthesized by the following method:

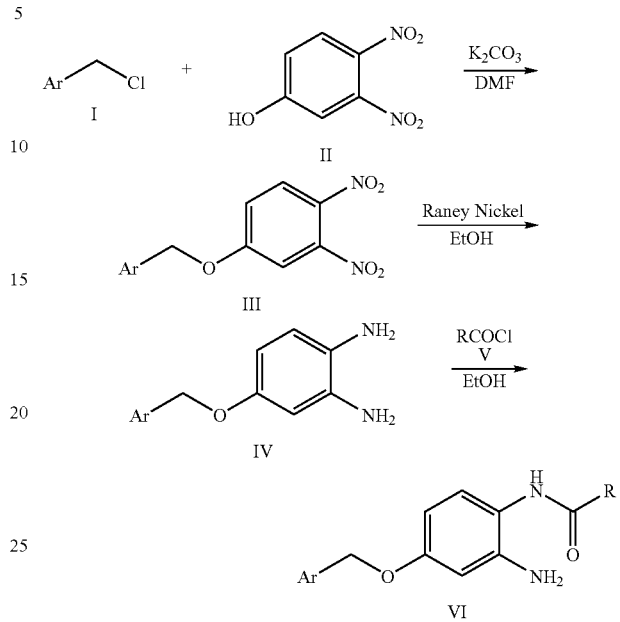

EXAMPLE 1

[2-Amino-4-(5-chloro-thiophen-2-ylmethoxy)-phenyl]-carbamic acid 2-methoxy-ethyl ester Step A: 4-(4-fluorobenzyloxy)-1,2-dinitrobenzene A stirred solution of 3,4-dinitrophenol (1 g, 5.4 mmol) in 30 ml of anhydrous dimethylformamide was treated with 4-fluorobenzyl chloride (0.86 g, 6.0 mmol) and potassium carbonate (1.13 g, 8.2 mmol). The reaction mixture was stirred at room temperature for 24 hours and then poured into 200 ml of ice-water and this mixture was stirred overnight. The solid was filtered and washed with water to give 1.2 g (76%) of tilted compound as a yellow solid after drying in vacuo. ¹H NMR (300 MHz, CDCl₃) δ: 8.04 (d, J=9.0 Hz, 1H), 7.40 (dd, J=5.4 and 8.7 Hz, 2H), 7.29 (d, J=2.7 Hz, 1H), 7.18 (dd, J=2.7 and 9.0 Hz, 1H), 7.12 (t, J=8.7 Hz, 2H), 5.16 (s, 2H).

Step B: 4-(4-fluorobenzyloxy)benzene-1,2-diamine

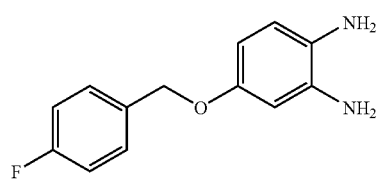

10 g of 4-(4-fluoro-benzyloxy)-2-nitro-aniline or 4-(4-Fluoro-benzyloxy)-1,2-dinitrobenzene was dissolved in 800 ml of methanol and 2 g of Raney Nickel was added. The resulting mixture was hydrogenated at room temperature under regular pressure for 5 hours. The reaction mixture was filtered with celite and washed with methanol. The filtrate was evaporated in vacuo to dryness to give the brown product, which gradually become black, in a quantitative yield.

Step C: N-(2-amino-4-(4-fluorobenzyloxy)phenyl)-3,3-dimethylbutanamide

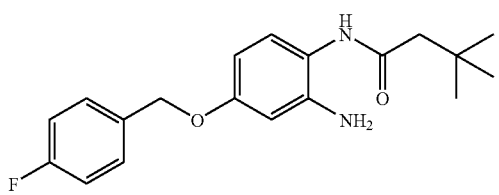 [SMILES: CC(C)(C)CC(=O)Nc1ccc(OCc2ccc(F)cc2)cc1N]

To a solution of 4-(4-fluoro-benzyloxy)-benzene-1,2-diamine (0.23 g, 1 mmol) and N,N-diisopropylethyllamine (0.21 ml, 1.2 mmol) in 8 ml of anhydrous ethanol was added dropwise tert-butylacetylchloride (111 µl, 1 mmol) at 4-5° C. in an ice-water bath. The reaction mixture was stirred for 30 min at 4-5° C. and for 3 hours at room temperature. The solvent was removed in vacuo and the residue was chromatographied (hexane/ethyl acetate, 2:1) to give the desired product as a white solid. $^1$H-NMR (300 MHz, DMSO-$d_6$): δ 8.94 (brs, 1H, exchangeable with $D_2O$, NH), 7.44 (dd, J=5.7 and 8.7 Hz, 2H), 7.18 (t, J=8.7 Hz, 2H), 6.92 (d, J=8.7 Hz, 1H), 6.34 (d, J=2.7 Hz, 1H), 6.18 (dd, J=8.7 and 2.7 Hz, 1H), 4.95 (s, 2H), 4.79 (brs, 2H, exchangeable with $D_2O$, $NH_2$), 2.13 (s, 2H), 1.00 (s, 9H). MS: 331 (M+1).

The following compounds were synthesized according to example 1:

EXAMPLE 2

N-(2-amino-4-(3,4-difluorobenzyloxy)phenyl)-3,3-dimethylbutanamide

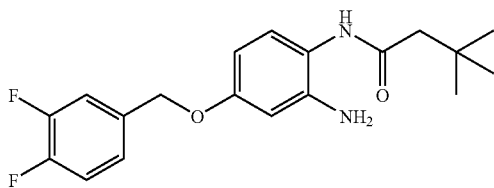 [SMILES: CC(C)(C)CC(=O)Nc1ccc(OCc2ccc(F)c(F)c2)cc1N]

$^1$H-NMR (300 MHz, DMSO-$d_6$): δ 8.94 (brs, 1H, exchangeable with $D_2O$, NH), 7.44 (m, 2H), 7.26 (m, 1H), 6.93 (d, J=8.7 Hz, 1H), 6.34 (d, J=2.7 Hz, 1H), 6.19 (dd, J=8.7, 2.7 Hz, 1H), 4.97 (s, 2H), 4.80 (brs, 2H, exchangeable with $D_2O$, $NH_2$), 2.13 (s, 2H), 1.00 (s, 9H). MS: 349 (M+1).

EXAMPLE 3

N-(2-amino-4-((5-chlorothiophen-2-yl)methoxy)phenyl)-3,3-dimethylbutanamide

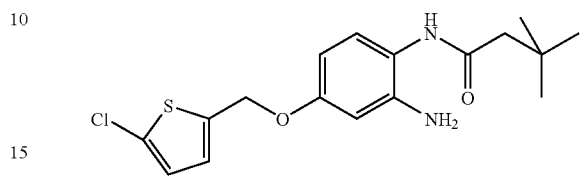

$^1$H-NMR (300 MHz, $CDCl_3$): δ 7.81 (brs, 1H, exchangeable with $D_2O$, NH), 7.02 (d, J=8.7 Hz, 1H), 6.84 (d, J=3.6, 1H), 6.77 (d, J=3.6 Hz, 1H), 6.71 (d, J=2.7 Hz, 1H), 6.51 (dd, J=8.7 and 2.7 Hz, 1H), 5.00 (s, 2H), 2.26 (s, 2H), 1.09 (s, 9H). MS: 353 (M+1).

EXAMPLE 4

N-(2-amino-4-(4-fluorobenzyloxy)phenyl)butyramide

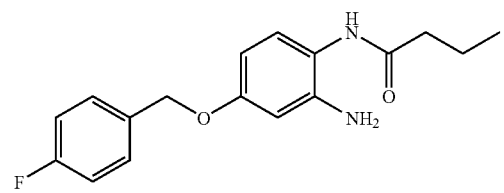 [SMILES: CCCC(=O)Nc1ccc(OCc2ccc(F)cc2)cc1N]

m/z=301 [M−1]$^−$.

EXAMPLE 5

N-(2-amino-4-(4-fluorobenzyloxy)phenyl)pivalamide

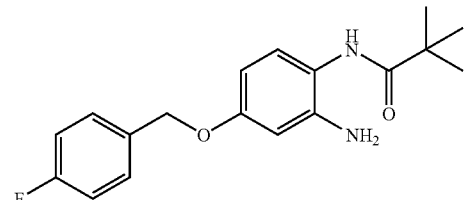

m/z=315 [M−1]$^−$.

EXAMPLE 6

N-(2-amino-4-(4-fluorobenzyloxy)phenyl)-2-(4-fluorophenyl)acetamide

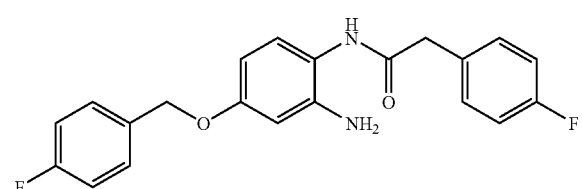

m/z=367 [M−1]$^−$.

EXAMPLE 7
N-(2-amino-4-(4-fluorobenzyloxy)phenyl)-2-phenylacetamide
EXAMPLE 8
N-(2-amino-4-(4-fluorobenzyloxy)phenyl)-2-phenoxyacetamide
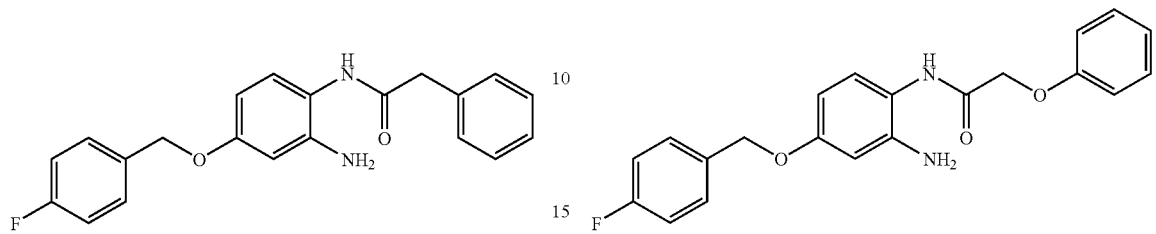
m/z=349 [M−1]⁻.
m/z=565 [M−1]⁻.
The compounds of formula B can be synthesized by the following general methods.
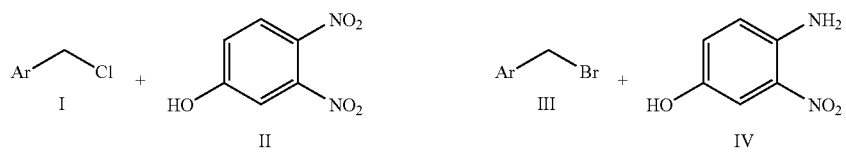
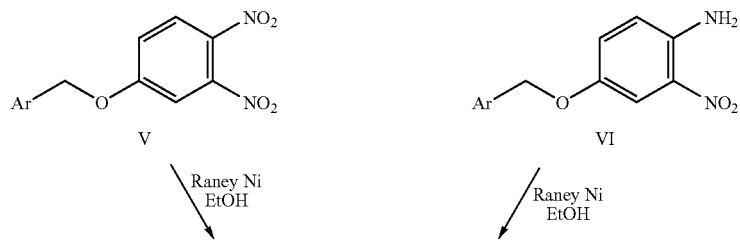
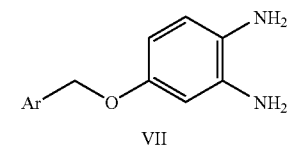
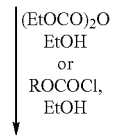
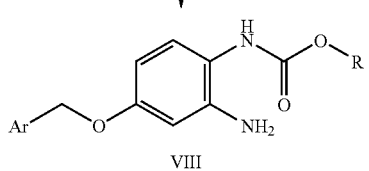

Typical Procedures for the Synthesis of the Diamine of General Formula B-VII:

General Procedure for the Synthesis of the Dinitro Compound of General Formula B-V A stirred solution of 3,4-dinitrophenol (1 eq) in anhydrous dimethylformamide (5 mL/mmole) was treated with the corresponding aryl chloride of general formula B-I (1.1 eq) and potassium carbonate (1.5 eq). The reaction mixture was stirred at room temperature for 24 hours and then poured into ice-water. This mixture was stirred overnight. The solid was filtered and washed with water to give the desired product which was dried in vacuo.

General Procedure for the Synthesis of the 2-Nitroalinine Compound of General Formula B-VI:

4-Amino-3-nitrophenol (1 eq) was dissolved in anhydrous dimethylformamide (1 mL/mmole) under argon and the mixture was cooled to 0° C. in an ice bath. Then a solution of potassium tert-butoxide in THF (1M, 1.1 eq) was added dropwise over 20 min. After the mixture had been stirred for 30 min at 0° C., a 0.3 M solution of the corresponding aryl bromide of general formula B-III in anhydrous dimethylformamide ((1.1 eq) was added dropwise. The reaction mixture was stirred at 0° C. for another 2 hours and then quenched with 10% ammonium chloride. The product was filtered and washed with water until the filtrate become colorless to give the desired product which was dried in vacuo.

General Procedure for the Synthesis of the 1,2-Diamine Derivatives of General Formula B-VII:

The 2-nitro-aniline derivative of general formula B-VI or the dinitrobenzene derivative of general formula B-V was dissolved in of methanol (80 mL/g) and a catalytic amount of Raney Nickel was added. The resulting mixture was hydrogenated at room temperature under regular pressure for 5 hours. The reaction mixture was filtered with celite and washed with methanol. The filtrate was evaporated in vacuum to dryness to give the brown product, which gradually become black, in a quantitative yield.

The following diamine derivatives were obtained using the general procedures described above (methods A or B):

4-(2-fluorobenzyloxy)benzene-1,2-diamine: m/z=231 [M−1]−

4-(2,4-difluorobenzyloxy)benzene-1,2-diamine: m/z=249 [M−1]−

4-(4-bromo-2-fluorobenzyloxy)benzene-1,2-diamine: m/z=310 [M−1]−

4-(3-fluorobenzyloxy)benzene-1,2-diamine: m/z=231 [M−1]−

4-(3,4-difluorobenzyloxy)benzene-1,2-diamine: m/z=249 [M−1]−

4-(3,5-difluorobenzyloxy)benzene-1,2-diamine: m/z=249 [M−1]−

4-(2-chloro-5-fluorobenzyloxy)benzene-1,2-diamine: m/z=265 [M−1]−

4-(2,5-dichlorobenzyloxy)benzene-1,2-diamine: m/z=282 [M−1]−

4-((4-chlorothiophen-2-yl)benzene-1,2-diamine: m/z=253 [M−1]−

4-((4-(trifluoromethyl)furan-2-yl)methoxy)benzene-1,2-diamine: m/z 271 [M−1]−

4-(4-fluorobenzyloxy)benzene-1,2-diamine: m/z=231 [M−1]−

4-(4-chlorobenzyloxy)benzene-1,2-diamine: m/z=247 [M−1]−

4-(4-methylbenzyloxy)benzene-1,2-diamine: m/z=227 [M−1]−

2-nitro-4-(4-(trifluoromethyl)benzene-1,2-diamine: m/z 281 [M−1]−

4-((4-amino-3-nitrophenoxy)benzene-1,2-diamine: m/z 238 [M−1]−

4-(4-(methylthio)benzyloxy)benzene-1,2-diamine: m/z=259 [M−1]− methyl 4-((3,4-diaminophenoxy)methyl)benzoate: m/z=271 [M−1]−

4-(3-fluorobenzyloxy)benzene-1,2-diamine: m/z=231 [M−1]−

4-(3-chlorobenzyloxy)benzene-1,2-diamine: m/z=247 [M−1]−

4-(3-methylbenzyloxy)benzene-1,2-diamine: m/z=227 [M−1]−

4-(3-(trifluoromethyl)benzyloxy)benzene-1,2-diamine: m/z=281 [M−1]−

3-((4-amino-3-nitrophenoxy)benzene-1,2-diamine: m/z=238 [M−1]−

4-(3-methoxybenzyloxy)benzene-1,2-diamine: m/z=243 [M−1]−

4-(naphthalen-2-ylmethoxy)benzene-1,2-diamine: m/z=263 [M−1]−

4-(2-fluorobenzyloxy)benzene-1,2-diamine: m/z=231 [M−1]−

4-(pyridin-3-ylmethoxy)benzene-1,2-diamine: m/z=214 [M−1]−

4-(benzyloxy)benzene-1,2-diamine: m/z=213 [M−1]−

4-(2-methylbenzyloxy)benzene-1,2-diamine: m/z=227 [M−1]−

4-(2-(trifluoromethyl)benzyloxy)benzene-1,2-diamine: m/z=281 [M−1]−

4-(2-(trifluoromethoxy)benzyloxy)benzene-1,2-diamine: m/z=291 [M−1]−

4-(4-fluorobenzyloxy)benzene-1,2-diamine: m/z=231 [M−1]−

Synthesis of the Carbamate Derivatives of General Formula B-VIII:

EXAMPLE 9

[2-Amino-4-(4-fluoro-benzyloxy)-phenyl]-carbamic acid ethyl ester 4-(4-Fluoro-benzyloxy)-benzene-1,2-diamine (0.23 g, 1 mmol) was dissolved in 8 ml of anhydrous ethanol and diethyl pyrocarbonate (144 μl, 1 mmol) was added dropwise at 4-5° C. in an ice-water bath. The reaction mixture was stirred for 30 min at 4-5° C. and for 3 hours at room temperature. The solvent was removed in vacuum and the residue was chromatographied (hexane/ethyl acetate, 2:1) to give pure product as a white solid. $^1$H NMR (300 MHz, CDCl$_3$) δ: 7.37 (dd, J=5.4 and 8.7 Hz, 2H), 7.06 (m, 3H), 6.38 (m, 2H), 4.96 (s, 2H), 4.20 (q, J=6.9 Hz, 2H), 3.82 (brs, 2H, exchangeable with D$_2$O), 1.29 (t, J=6.9 Hz. 3H).

The following compounds were synthesized by the above procedure.

EXAMPLE 10

Ethyl 2-amino-4-(2-fluorobenzyloxy)phenylcarbamate m/z=303 [M−1]⁻.

EXAMPLE 11

Ethyl 2-amino-4-(2,4-difluorobenzyloxy)phenylcarbamate m/z=321 [M−1]⁻.

EXAMPLE 12

Ethyl 2-amino-4-(4-bromo-2-fluorobenzyloxy)phenylcarbamate m/z=382 [M−1]⁻.

EXAMPLE 13

Ethyl 2-amino-4-(3-fluorobenzyloxy)phenylcarbamate m/z=303 [M−1]⁻.

EXAMPLE 14

Ethyl 2-amino-4-(3,4-difluorobenzyloxy)phenylcarbamate m/z=321 [M−1]⁻.

EXAMPLE 15

Ethyl 2-amino-4-(3,5-difluorobenzyloxy)phenylcarbamate m/z=3211 [M−1]⁻.

EXAMPLE 16

Ethyl 2-amino-4-(2-chloro-5-fluorobenzyloxy)phenylcarbamate m/z=337 [M−1]⁻.

EXAMPLE 17

Ethyl 2-amino-4-(2,5-dichlorobenzyloxy)phenylcarbamate m/z=3541 [M−1]⁻.

EXAMPLE 18

Ethyl 2-amino-4-((4-chlorothiophen-2-yl)methoxy) phenylcarbamate

¹H NMR (300 MHz, CDCl₃): δ 7.07 (d, J=9.0 Hz, 1H), 6.84 (d, J=3.9 Hz, 1H), 6.78 (d, J=3.9 Hz, 1H), 6.37 (m, 2H), 6.18 (brs, 1H), 5.03 (s, 2H), 4.19 (q, J=7.2 Hz, 2H), 3.54 (brs, 2H, exchangeable with D₂O, NH₂), 1.28 (t, J=6.9 Hz, 3H). m/z=325 [M−1]⁻.

EXAMPLE 19

Ethyl 2-amino-4-((4-(trifluoromethyl)furan-2-yl) methoxy)phenylcarbamate m/z=343 [M−1]⁻.

EXAMPLE 20

Ethyl 2-amino-4-(4-chlorobenzyloxy)phenylcarbamate m/z=319 [M−1]⁻.

EXAMPLE 21

Ethyl 2-amino-4-(4-methylbenzyloxy)phenylcarbamate m/z=299 [M−1]⁻.

EXAMPLE 22

Ethyl 2-amino-4-(4-(trifluoromethyl)benzyloxy) phenylcarbamate m/z=353 [M−1]⁻.

EXAMPLE 23

Ethyl 2-amino-4-(4-cyanobenzyloxy)phenylcarbamate m/z=310 [M−1]⁻.

EXAMPLE 24

Ethyl 2-amino-4-(4-(methylthio)benzyloxy)phenylcarbamate m/z=331 [M−1]⁻.

EXAMPLE 25

Methyl 4-((3-amino-4-(ethoxycarbonylamino)phenoxy)methyl)benzoate m/z=343 [M−1]⁻.

EXAMPLE 26

Ethyl 2-amino-4-(3-fluorobenzyloxy)phenylcarbamate m/z=303 [M−1]⁻.

EXAMPLE 27

Ethyl 2-amino-4-(3-chlorobenzyloxy)phenylcarbamate m/z=319 [M−1]⁻.
¹H-NMR (300 MHz, DMSO-d₆): δ 8.34 (brs, 1H, exchangeable with D₂O, NH), 7.40 (m, 4H), 6.94 (d, J=7.5

Hz, 1H), 6.31 (d, J=2.7 Hz, 1H), 6.16 (dd, J=7.5 and 2.7 Hz, 1H), 4.98 (s, 2H), 4.86 (brs, 2H, exchangeable with D$_2$O, NH$_2$), 4.02 (q, J=7.2 Hz, 2H), 1.18 (t, J=7.2 Hz, 3H).

EXAMPLE 28

Ethyl 2-amino-4-(3-methylbenzyloxy)phenylcarbamate m/z=299 [M−1]$^-$.

EXAMPLE 29

Ethyl 2-amino-4-(3-(trifluoromethyl)benzyloxy) phenylcarbamate m/z=353 [M−1]$^-$.

EXAMPLE 30

Ethyl 2-amino-4-(3-cyanobenzyloxy)phenylcarbamate m/z=310 [M−1]$^-$.

EXAMPLE 31

Ethyl 2-amino-4-(3-methoxybenzyloxy)phenylcarbamate m/z=315 [M−1]$^-$.

EXAMPLE 32

Ethyl 2-amino-4-(naphthalen-2-ylmethoxy)phenylcarbamate m/z=335 [M−1]$^-$.

EXAMPLE 33

Ethyl 2-amino-4-(2-fluorobenzyloxy)phenylcarbamate m/z=303 [M−1]$^-$.

EXAMPLE 34

Ethyl 2-amino-4-(pyridin-3-ylmethoxy)phenylcarbamate m/z=286 [M−1]$^-$.

EXAMPLE 35

Ethyl 2-amino-4-(benzyloxy)phenylcarbamate m/z=285 [M−1]$^-$.

EXAMPLE 36

Ethyl 2-amino-4-(2-methylbenzyloxy)phenylcarbamate m/z=299 [M−1]$^-$.

EXAMPLE 37

Ethyl 2-amino-4-(2-(trifluoromethyl)benzyloxy) phenylcarbamate m/z=353 [M−1]$^-$.

EXAMPLE 38

Ethyl 2-amino-4-(2-(trifluoromethoxy)benzyloxy) phenylcarbamate m/z=399 [M−1]$^-$

EXAMPLE 39

[2-Amino-4-(4-fluoro-benzyloxy)-phenyl]-carbamic acid propyl ester

A solution of 4-(4-fluoro-benzyloxy)-benzene-1,2-diamine (0.23 g, 1 mmol) and N,N-diisopropylethyllamine (0.21 ml, 1.2 mmol) in 8 ml of anhydrous ethanol was added dropwise propyl chloroformate (112 μl, 1 mmol) at 4-5° C. in an ice-water bath. The reaction mixture was stirred for 30 min at 4-5° C. and for 3 hours at room temperature. The solvent was removed in vacuum and the residue was chromatographied (hexane/ethyl acetate, 2:1) to give pure product as a white solid. $^1$H NMR (300 MHz, DMSO-d$_6$) δ: 8.35 (brs, 1H, exchangeable with D$_2$O), 7.44 (dd, J=5.7 and 8.7 Hz, 2H), 7.18 (t, J=8.7 Hz, 2H), 6.94 (d, J=7.2 Hz, 1H), 7.31 (d, J=2.7 Hz, 1H), 6.16 (dd, J=2.7 and 8.4 Hz, 1H), 4.94 (s, 2H), 4.85 (brs, 2H, exchangeable with D$_2$O), 3.94 (t, J=6.9 Hz, 2H), 1.58 (m, 2H), 0.89 (t, J=6.9 Hz. 3H), m/z=317 [M−1]$^-$.

The following compounds were synthesized by the above procedure with 4-(4-fluoro-benzyloxy)-benzene-1,2-diamine and the corresponding chloroformate.

EXAMPLE 40

Methyl 2-amino-4-(4-fluorobenzyloxy)phenylcarbamate m/z=289 [M−1]$^-$.

EXAMPLE 41

Ethyl 2-amino-4-(4-fluorobenzyloxy)phenylcarbamate m/z=303 [M−1]$^-$.

EXAMPLE 42

Butyl 2-amino-4-(4-fluorobenzyloxy)phenylcarbamate m/z=331 [M−1]$^-$.

EXAMPLE 43

Hexyl 2-amino-4-(4-fluorobenzyloxy)phenylcarbamate m/z=359 [M−1]$^-$.

EXAMPLE 44

Octyl 2-amino-4-(4-fluorobenzyloxy)phenylcarbamate m/z=381 [M−1]⁻.

EXAMPLE 45

Isopropyl 2-amino-4-(4-fluorobenzyloxy)phenylcarbamate m/z=317 [M−1]⁻.

EXAMPLE 46

Isobutyl 2-amino-4-(4-fluorobenzyloxy)phenylcarbamate m/z=331 [M−1]⁻.

EXAMPLE 47

Allyl 2-amino-4-(4-fluorobenzyloxy)phenylcarbamate m/z=315 [M−1]⁻.

EXAMPLE 48

But-3-enyl 2-amino-4-(4-fluorobenzyloxy)phenylcarbamate m/z=329 [M−1]⁻, $^1$H-NMR (300 MHz, DMSO-$d_6$): δ 8.38 (brs, 1H, exchangeable with $D_2O$, NH), 7.44 (dd, J=5.7 and 8.7 Hz, 2H), 7.18 (t, J=8.7 Hz, 2H), 6.93 (d, J=8.1 Hz, 1H), 6.31 (d, J=2.7 Hz, 1H), 6.16 (dd, J=8.1 and 2.7 Hz, 1H), 5.81 (m, 1H), 5.11 (d, J=17.7 Hz, 1H), 5.05 (d, J=10.8 Hz, 1H), 4.94 (s, 2H), 4.84 (brs, 2H, exchangeable with $D_2O$, $NH_2$), 4.04 (t, J=6.6 Hz, 2H), 2.34 (q, J=6.3 Hz, 2H).

EXAMPLE 49

Cyclopentyl 2-amino-4-(4-fluorobenzyloxy)phenylcarbamate m/z=343 [M−1]⁻.

EXAMPLE 50

Neopentyl 2-amino-4-(4-fluorobenzyloxy)phenylcarbamate m/z=345 [M−1]⁻.

EXAMPLE 51

Prop-2-ynyl 2-amino-4-(4-fluorobenzyloxy)phenylcarbamate m/z=313 [M−1]⁻.

EXAMPLE 52

But-3-ynyl 2-amino-4-(4-fluorobenzyloxy)phenylcarbamate m/z=327 [M−1]⁻.

EXAMPLE 53

2-Fluoroethyl 2-amino-4-(4-fluorobenzyloxy)phenylcarbamate m/z=321 [M−1]⁻.

EXAMPLE 54

But-2-ynyl 2-amino-4-(4-fluorobenzyloxy)phenylcarbamate m/z=327 [M−1]⁻.

EXAMPLE 55

2-Chloroethyl 2-amino-4-(4-fluorobenzyloxy)phenylcarbamate m/z=337 [M−1]⁻.

EXAMPLE 56

2-Methoxyethyl 2-amino-4-(4-fluorobenzyloxy)phenylcarbamate m/z=333 [M−1]⁻.

EXAMPLE 57

Benzyl 2-amino-4-(4-fluorobenzyloxy)phenylcarbamate m/z=365 [M−1]⁻.

EXAMPLE 58

2-Chlorobenzyl 2-amino-4-(4-fluorobenzyloxy)phenylcarbamate m/z=399 [M−1]⁻.

EXAMPLE 59

2-Methoxyethyl 2-amino-4-(4-fluorobenzyloxy)phenylcarbamate m/z=333 [M−1]⁻. $^1$H-NMR (300 MHz, DMSO-$d_6$): δ 8.48 (brs, 1H, exchangeable with $D_2O$, NH), 7.44 (dd, J=5.7 and 8.7 Hz, 2H), 7.18 (t, J=8.7 Hz, 2H), 6.94 (d, J=8.1 Hz, 1H), 6.31 (d, J=2.7 Hz, 1H), 6.16 (dd, J=8.1 and 2.7 Hz, 1H), 4.94 (s, 2H), 4.86 (brs, 2H, exchangeable with $D_2O$, $NH_2$), 4.11 (t, J=4.5 Hz, 2H), 3.51 (t, J=4.5 Hz, 2H), 3.25 (s, 3H).

EXAMPLE 60

2-Methoxyethyl 2-amino-4-(3,4-difluorobenzyloxy)phenylcarbamate m/z=351 [M−1]⁻.

EXAMPLE 63

2-Methoxyethyl 2-amino-4-((5-chlorothiophen-2-yl)methoxy)phenylcarbamate m/z=355 [M−1]− $^1$H-NMR (300 MHz, DMSO-d$_6$): δ 8.60 (brs, 1H, exchangeable with D$_2$O, NH), 7.02 (d, J=8.7 Hz, 1H), 7.02 (d, J=3.6, 1H), 7.01 (d, J=3.6 Hz, 1H), 6.37 (d, J=2.7 Hz, 1H), 6.28 (dd, J=8.7 and 2.7 Hz, 1H), 5.10 (s, 2H), 4.12 (t, J=4.5 Hz, 2H), 3.52 (t, J=4.5, 2H), 3.25 (s, 3H).

EXAMPLE 64

Ethyl 2-amino-4-(4-fluorobenzyloxy)phenylcarbamate m/z=303 [M−1]−.

EXAMPLE 65

Isopropyl 2-amino-4-(4-fluorobenzyloxy)phenylcarbamate m/z=317 [M−1]−.

EXAMPLE 66

Propyl 2-amino-4-(4-fluorobenzyloxy)phenylcarbamate m/z=317 [M−1]−.

EXAMPLE 67

Butyl 2-amino-4-(4-fluorobenzyloxy)phenylcarbamate m/z=331 [M−1]−.

EXAMPLE 68

2-Chloroethyl 2-amino-4-(4-fluorobenzyloxy)phenylcarbamate m/z=337 [M−1]−.

EXAMPLE 69

3-Chloropropyl 2-amino-4-(4-fluorobenzyloxy)phenylcarbamate m/z=351 [M−1]−.

EXAMPLE 70

2-Methoxyethyl 2-amino-4-(4-fluorobenzyloxy)phenylcarbamate m/z=333 [M−1]−.

EXAMPLE 71

But-2-ynyl 2-amino-4-(4-fluorobenzyloxy)phenylcarbamate m/z=329 [M−1]−.

The furanyl, thienyl and benzothienyl compounds of the invention can be prepared by reactions analogous to scheme 1 using the corresponding methylchlorides, which can be prepared from the corresponding substituted methanols. Preparation of thienyl- and furanyl- and benzo-furanyl methanols can be performed as described in WO 2004/58739.

Biological Results

Compounds of the following formula were assayed as KCNQ 2/3 activators by measuring rhubidium release.

Methods:

PC-12 cells were grown at 37° C. and 5% CO$_2$ in DMEM/F12 Medium supplemented with 10% horse serum, 5% fetal bovine serum, 2 mM glutamine, 100 U/ml penicillin, 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated and the cells were washed once with 0.2 ml in wash buffer (25 mM Hepes, pH 7.4, 150 mM NaCl, 1 mM MgCl$_2$, 0.8 mM NaH$_2$PO$_4$, 2 mM CaCl$_2$). The cells were then loaded with 0.2 ml Rb$^+$ loading buffer (wash buffer plus 5.4 mM RbCl$_2$, 5 mM glucose) and incubated at 37° C. for 2 h. Attached cells were quickly washed three times with buffer (same as Rb$^+$ loading buffer, but containing 5.4 mM KCl instead of RbCl) to remove extracellular Rb$^+$. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for Rb$^+$ contents by atomic absorption spectroscopy (see below), they were stored at 4° C. without any negative effects on subsequent Rb$^+$ analysis.

The concentration of Rb$^+$ in the supernatants (Rb$^+$ sup) and cell lysates (Rb$^+_{Lys}$) was quantified using an ICR8000 flame atomic absorption spectrometer (Aurora Biomed Inc., Vancouver, B.C.) under conditions defined by the manufacturer. One 0.05 ml samples were processed automatically from microtiter plates by dilution with an equal volume of Rb$^+$ sample analysis buffer and injection into an air-acetylene flame. The amount of Rb$^+$ in the sample was measured by absorption at 780 nm using a hollow cathode lamp as light source and a PMT detector. A calibration curve covering the range 0-5 mg/L Rb$^+$ in sample analysis buffer was generated with each set of plates. The percent Rb$^+$ efflux (F) was defined by $$F=[Rb^+_{Sup}/(Rb^+_{Sup}+Rb^+_{Lys})]\times 100\%$$

The effect (E) of a compound was defined by: $E=[(F_c-F_b)/(F_s-F_b)]\times 100\%$ where the $F_c$ is the efflux in the presence of compound in depolarization buffer, $F_b$ is the efflux in basal buffer, and $F_s$ is the efflux in depolarization buffer, and $F_c$ is the efflux in the presence of compound in depolarization buffer. The effect (E) and compound concentration relationship was plotted to calculate an $EC_{50}$ value, a compound's concentration for 50% of maximal Rb$^+$ efflux.

Results:

Compounds of formula A according to the formula below were tested with the results given in the table below.

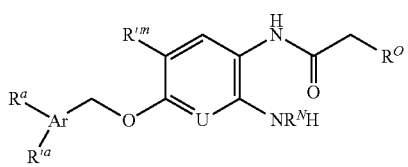

The results are given in the table below. For comparison, data for retigabine and flupirtine are also provided.

| Compound | EC$_{50}$ (μM) | Ar | R$^a$ | R$^{ia}$ | U | R$^O$ | R$^N$ |
|---|---|---|---|---|---|---|---|
| flupirtine | B | | | | | | |
| retigabine | A | | | | | | |
| I | A | phenyl | 4-F | H | =CH | neopentyl | H |
| II | A | phenyl | 4-F | 3-F | =CH | neopentyl | H |
| III | A | 2-thienyl | 5-Cl | H | =CH | neopentyl | H |

Code: A, EC$_{50}$ < 2.0 μM; B, EC$_{50}$ ≤ 15 μM; C, EC$_{50}$ > 30 μM.

Results: Compounds of formula B according to the generic formula below were tested with the results given in the table below.

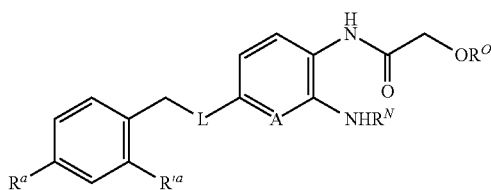

The results are given in the table below. For comparison, data for flupirtine and retigabine are also provided.

| Compound | EC$_{50}$ (μM) | A | L | R$^O$ | R$^N$ | R$^{ia}$ | R$^a$ |
|---|---|---|---|---|---|---|---|
| flupirtine | B | —N— | —NH— | Et | H | H | F |
| retigabine | A | —CH— | —NH— | Et | H | H | F |
| IV | A | —CH— | —O— | Et | H | H | F |
| V | C | —CH— | —O— | Et | EtOC(=O)— | H | F |
| VI | C | —CH— | —O— | Et | H | CF$_3$ | H |
| IV | B | —CH— | —O— | Et | H | H | Me |
| V | B | —CH— | —O— | Me | H | H | F |

Code: A, EC$_{50}$ < 2.0 μM; B, EC$_{50}$ ≤ 15 μM; C, EC$_{50}$ > 30 μM.

What is claimed is:

1. A compound of formula A

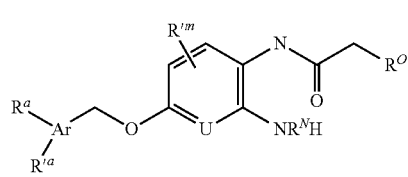

where Ar is phenyl U=—C(R$^m$)=—; R$^a$ and R$^{ia}$ are, independently, H, F, Cl, methyl, methoxy, fluoromethyl, difluoromethyl, or trifluoromethyl; R$^m$ is H, F, Cl, methyl, fluoromethyl, difluoromethyl, trifluoromethyl or methoxy; R$^{im}$ is F, Cl, fluoromethyl, difluoromethyl, trifluoromethyl or methoxy; R$^N$ is H or C$_1$-C$_4$ alkyl, which may be straight-chain, branched, or cyclic; and R$^O$ is H, isopropyl, sec-butyl, or straight-chain C$_1$-C$_8$ alkyl, alkenyl, or alkynyl, any of which may be substituted by methyl, fluoro, chloro methoxy, phenyl, or benzoyloxy, where the methyl, methoxy, phenyl, and benzyl groups are optionally substituted with one or two fluorine atoms or one or two chlorine atoms.

2. The compound of claim 1, where R$^a$ is CF$_3$, F, or Cl and R$^{ia}$ is H or F.

3. The compound of claim 2, where R$^{im}$ is F and R$^N$ is H or methyl.

4. The compound of claim 3, where R$^O$ is C$_1$-C$_4$ alkyl, C$_1$-C$_4$ alkenyl, or CH$_3$O—(CH$_2$)$_n$CH$_2$—, where n is 0, 1, 2, or 3.

5. The compound of claim 1, where R$^O$ is selected from the group methyl, ethyl, propyl, butyl sec-butyl, pentyl, hexyl, 2-chloroethyl, 3-chloropropyl, 4-chlorobutyl, 2-fluoroethyl, 3-fluoropropyl, 4-fluorobutyl, 2,2,2-trifluoroethyl, 2,2,2-trichloroethyl, methoxyethyl, benzyloxyethyl, benzyl, o-chlorobenzyl, o-, o'-dichlorobenzyl o-fluorobenzyl, and o-, o'-difluorobenzyl.

6. A composition comprising a pharmaceutically acceptable carrier and one or more of the following: a compound of claim 1; a salt or ester thereof.

* * * * *